(12) United States Patent
Stahl et al.

(10) Patent No.: US 9,359,391 B2
(45) Date of Patent: *Jun. 7, 2016

(54) SELECTIVE C—O BOND CLEAVAGE OF OXIDIZED LIGNIN AND LIGNIN-TYPE MATERIALS INTO SIMPLE AROMATIC COMPOUNDS

(71) Applicant: Wisconsin Alumni Research Foundation, Madison, WI (US)

(72) Inventors: Shannon S. Stahl, Madison, WI (US); Joshua Coon, Madison, WI (US); Alireza Rahimi, Madison, WI (US); Arne Ulbrich, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 133 days.

This patent is subject to a terminal disclaimer.

(21) Appl. No.: 14/212,173

(22) Filed: Mar. 14, 2014

(65) Prior Publication Data

US 2015/0259368 A1 Sep. 17, 2015

(51) Int. Cl.
| | | |
|---|---|---|
| *C08H 8/00* | (2010.01) | |
| *C07B 41/06* | (2006.01) | |
| *C08J 3/00* | (2006.01) | |
| *C07G 1/00* | (2011.01) | |
| *C08H 7/00* | (2011.01) | |

(52) U.S. Cl.
CPC . *C07G 1/00* (2013.01); *C07B 41/06* (2013.01); *C08H 6/00* (2013.01)

(58) Field of Classification Search
CPC .............. C08H 8/00; C08J 3/00; C07B 41/06
See application file for complete search history.

(56) References Cited

U.S. PATENT DOCUMENTS

| | | | | |
|---|---|---|---|---|
| 3,726,850 | A * | 4/1973 | Detroit | 30/501 |
| 4,055,601 | A * | 10/1977 | Ehmann | 568/390 |
| 4,133,385 | A * | 1/1979 | Kalfoglou | 166/270.1 |
| 5,094,295 | A * | 3/1992 | Morrow | 166/270.1 |
| 5,446,133 | A * | 8/1995 | Detroit | 530/500 |
| 6,258,209 | B1 * | 7/2001 | Stohrer et al. | 162/65 |
| 8,969,534 | B2 * | 3/2015 | Stahl et al. | 530/500 |
| 2012/0107886 | A1 * | 5/2012 | Albizati et al. | 435/146 |
| 2014/0235838 | A1 * | 8/2014 | Stahl et al. | 530/504 |
| 2014/0249300 | A1 * | 9/2014 | Bozell et al. | 530/507 |

FOREIGN PATENT DOCUMENTS

| | | |
|---|---|---|
| WO | WO 2011003029 A2 * | 1/2011 |
| WO | WO 2011/022511 A2 | 2/2011 |
| WO | WO 2013/173316 A1 | 11/2013 |
| WO | WO 2014/038989 A1 | 3/2014 |
| WO | WO 2014/039002 A1 | 3/2014 |

OTHER PUBLICATIONS

Aellig et al., Acid-Catalyzed Decomposition of the Benzyl Nitrite Intermediate in HNO$_3$-Mediated Aerobic Oxidation of Benzyl Alcohol, *ChemCatChem* 2012, 4, 525-529.
Badamali et al., Co(salen)/SBA-15 catalysed oxidation of a β-O-4 phenolic dimer under microwave irradiation, *Catalysis Communications* 2011, 12, 993-995.
Brink et al., Catalytic Conversions I Water. Part 23: Steric Effects and Increased Substrate Scope in the Palladium-Neocuproine Catalyzed Aerobic Oxidation of Alcohols in Aqueous Solvents, *Adv. Synth. Catal.* 2003, 345, 1341-1352.
Buendia et al., Preparation of Diastereomerically Pure Dilignol Model Compounds, *Chem. Eur. J.* 2011, 17, 13877-13822.
Chheda et al., Liquid-Phase Catalytic Processing of Biomass-Derived Oxygenated Hydrocarbons to Fuels and Chemicals, *Angew. Chem. Int. Ed.* 2007, 46, 7164-7183.
Cho et al., Nature and Kinetic Analysis of Carbon—Carbon Bond Fragmentation Reactions of Cation Radicals Derived from SET-Oxidation of Lignin Model Compounds, *J. Org. Chem.* 2010, 75, 6549-6562.
Collinson et al., The Catalytic oxidation of biomass to new materials focusing on starch, cellulose and lignin, *Coord. Chem. Rev.* 2010, 254, 1854-1870.
Crestini et al., Immobilized methyltrioxo rhenium (MTO)/H$_2$O$_2$ systems for the oxidation of lignin and lignin model compounds, *Biorg. Med. Chem.* 2006, 14, 5292-5302.
Corma et al., Chemical Routes for the Transformation of Biomass into Chemicals, *Chem. Rev.* 2007, 107, 2411-2502.
Cui et al., Biomimetic degradation of lignin, *J. Biotechnol.* 1993, 30, 15-26.
Cui et al., Metallophthalocyanines as Possible Lignin Peroxidase Models, *Bioorg. Med. Chem.* 1995, 3, 471-477.
Cutulic et al., Metal-Free Reductive Cleavage of C—O σ-bonds in Acyloin Derivatives by an Organic Neutral Super-Electron-Donor, *J. Org. Chem.* 2009, 74, 8713-8718.
Gosselink et al., Co-ordination network for lignin—standardisation, production and applications adapted to market requirements (EUROLIGNIN), *Ind. Crops Prod.* 2004, 20, 121-129.
Grabber, J. H., How Do Lignin Compositions, Structure, and Cross-Linking Affect Degradability? A Review of Cell Wall Model Studies, *Crop Sci.* 2005, 45, 820-831.
Hanson et al., Aerobic Oxidation of Lignin Models Using a Base metal Vanadium Catalyst, *Inorg. Chem.* 2010, 49, 5611-5618.
Hanson et al., C—C or C—O Bond Cleavage in a Phenolic Lignin Model Compound: Selectivity Depends on Vanadiu, Catalyst, *Angew. Chem. Int. Ed.* 2012, 51, 3410-3413.

(Continued)

*Primary Examiner* — Liam J Heincer
(74) *Attorney, Agent, or Firm* — Joseph T. Leone, Esq.; DeWitt Ross & Stevens S.C.

(57) ABSTRACT

A method to cleave C—C and C—O bonds in β-O-4 linkages in lignin or lignin sub-units is described. The method includes oxidizing at least a portion of secondary benzylic alcohol groups in β-O-4 linkages in the lignin or lignin sub-unit to corresponding ketones and then leaving C—O or C—C bonds in the oxidized lignin or lignin sub-unit by reacting it with an organic carboxylic acid, a salt of an organic carboxylic acids, and/or an ester of an organic carboxylic acids. The method may utilize a metal or metal-containing reagent or proceed without the metal or metal-containing reagent.

5 Claims, 10 Drawing Sheets

(56) References Cited

OTHER PUBLICATIONS

Herrmann et al., Methyltrioxorphenium: oxidative cleavage of CC-double bonds and its application in a highly efficient synthesis of vanillin from biological waste, *J. Mol. Catal. A: Chem.* 2000, 153, 49-52.
Hocking, M.B., Vanillin: Synthetic Flavoring from Spent Sulfite Liquor, *J. Chem. Educ.* 1997, 74, 1055-1059.
Hurrell et al., Photochemistry of lignin model compounds on solid supports, *Can. J. Chem.* 1993, 71, 1340-1348.
Ibrahim et al., Synthesis of *erythro* and *threo* Forms of Lignin Models of the Arylglycerol β-Guaiacyl Ether Type, *Acta. Chem. Scand.* 1994, 48, 149-151.
Jeena et al., Convenient photooxidation of alcohols using dye sensitized zinc oxide in combination with silver nitrate and TEMPO, *Chem. Commun.* 2012, 48, 299-301.
Kandanarachchi et al., Model Compound Studies of the β-O-4 Linkage in Lignin: Absolute Rate Expressions for β-Scission of Phenoxyl Radical from 1-Phenyl-2-phenoxyehtanol-1-yl Radical, *J. Org. Chem.* 2002, 23, 7937-7945.
Kuang et al., A Nitric Acid-Assisted Carbon-Catalyzed Oxidation System with Nitroxide Radical Cocatalysts as an Efficient and Green Protocol for Selective Aerobic Oxidation of Alcohols, *Adv. Synth. Catal.* 2010, 352, 2635-2642.
Kumar et al., Methods for Pretreatment of Lignocellulosic Biomass for Efficient Hydrolysis and Biofuel Production, *Ind. Eng. Chem. Res.* 2009, 48, 3713-3729.
Larsson et al., Gaschromatographische Analyse von Ligninoxydations-produkten, *Acta. Chem. Scand.* 1971, 25, 647-662.
Ma et al., Development of a General and Practical Iron Nitrate/TEMPO-Catalyzed Aerobic Oxidation of Alcohols to Aldehydes/Ketones: Catalysis with table Salt, *Adv. Synth. Catal.* 2011, 353, 1005-1017.
Martínz et al., Monolignol acylation and lignin structure in some nonwoody plants: A 2D NMR study, *Phytochemistry* 2008, 69, 2831-2843.
Naimi-Jamal et al., Sustainable Synthesis of Aldehydes, Ketones or Acids from Neat Alcohols Using Nitrogen Dioxide Gas, and Related Reactions, *ChemSusChem* 2009, 2, 83-88.
Nichols et al., Catalytic C—O Bond Cleavage of 2-Aryloxy-1-arylethanols and Its Application to the Depolymerization of Lignin-Related Polymers, *J. Am. Chem. Soc.* 2010, 132, 12554-12555.
Nillar et al., Oxidation of Hardwood Kraft-Lignin to the Phenolic Derivatives, Nitrobenzene and Copper Oxide as Oxidants, *J. Wood Chem. Technol.* 1997, 17, 259-285.
Pardini et al., Electroorganic Reactions. 38, Mechanism of Electrooxidative Cleavage of Lignin Model Dimers, J. Org. Chem. 1991, 56, 7305-7313.
Partenheimer, W., The Aerobic Oxidative Cleavage of Lignin to Produce Hydroxy-aromatic Benzaldehydes and Carboxylic Acids via Metal/Bromide Catalysts in Acetic/Water Mixtures, *Adv. Synth. Catal.* 2009, 351, 456-466.
Pepper et al., Lignin oxidation. Preferential use of cupric oxide, *Can. J. Chem.* 1967, 45, 3009-3012.
Philippidis et al., Study of the Enzymatic Hydrolysis of Cellulose for Production of Fuel Ethanol by the Simultaneous Saccharification and Fermentation Process, *Biotechnol. Bioeng.* 1993, 41, 846-853.
Ralph, J., Encyclopedia of Life Sciences, Lignins, © 2007 John Wiley & Sons, Ltd. (Book).
Sarkanen et al., Lignins, Occurrence, Formation, Structure and Reactions; Wiley-Interscience, New York, 1971 (Book).
Sawaki et al., Mechanism of C—C Cleavage of Cyclic 1,2-Diketones with Alkaline Hydrogen Peroxide. The Acyclic Mechanism and Its application to the Basic Autoxidation of Pyrogallol, *J. Am. Chem. Soc.* 1983, 105, 5035-5040.
Shibuya et al., Highly Efficient, Organocatalytic Aerobic Alcohol Oxidation, *J. Am. Chem. Soc.* 2011, 133, 6497-6500.
Son et al., Non-Oxidative Vanadium-Catalyzed C—O Bond Cleavage: Application to Degradation of Lignin Model Compounds, *Angew. Chem. Int. Ed.* 2010, 49, 3791-3794.
Steinhoff et al., Mechanistic Study of Alcohol Oxidation by the $Pd(OAc)_2/O_2$/DMSO Catalyst System and Implications for the Development of Improved Aerobic Oxidation Catalysts, *J. Am. Chem. Soc.* 2002, 124, 766-767.
Steinhoff et al., Mechanism of $Pd(OAc)_2$/DMSO-Catalyzed Aerobic Alcohol Oxidation: Mass-Transfer-Limitation Effects and Catalyst Decomposition Pathways, *J. Am. Chem. Soc.* 2006, 128, 4348-4355.
Strazzolini et al., Oxidation of Benzylic Alcohols and Ethers to Carbonyl Derivatives by Nitric Acid in Dichloromethane, *Eur. J. Org. Chem.* 2003, 2003, 526-536.
Tanielyan et al., Transition Metal Free Catalytic Aerobic Oxidation of Methyl-α-D-Glucopyranioside Under Mild Conditions Using Stable Nitroxyl Free Radicals, *Top Catal* 2012, 55, 556-564.
Tarabanko et al., On the Mechanism of Vanillin Formation in the Catalytic Oxidation of Lignin With Oxygen, *React. Kinet. Catal. Lett.* 1995, 55, 161-170.
U.S. Energy Information Administration/Annual *Energy Review* 2011, Washington, DC 20585.
Vanholme et al., Lignin Biosynthesis and Structure, *Plant Physiology*, 2010, 153, 895-905.
Wang et al., TEMPO/HCl/NaNO2 Catalyst: A Transition-Metal-Free Approach to Efficient Aerobic Oxidation of Alcohols to Aldehydes and ketones Under Mild Conditions, *Chem. Eur. J.* 2008, 14, 2679-2685.
Yamamura et al., Microscale alkaline nitrobenzene oxidation method for high-throughput determination of lignin aromatic components, *Plant Biotech.* 2010, 27, 305-310.
Zakzeski et al., The Catalytic Valorization of Lignin for the Production of Renewable Chemicals, *Chem, Rev.* 2010, 110, 3552-3599.
Zhang et al., Wet Aerobic Oxidation of Lignin into Aromatic Aldehydes Catalysed by a Perovskite-type Oxide: $LaFe_{1-x}Cu_xO_3$, *Molecules* 2009, 14, 2747-2757.
Zhang et al., Aerobic Oxidation Reactions Catalyzed by Vanadium Complexes of Bis(Phenolate) Ligands, *Inorg. Chem.* 2012, 51(13), 7354-7361.
Rahimi, et al., "Chemoselective Metal-Free Aerobic Alcohol Oxidation in Lignin," Journal of the American Chemical Society, Apr. 9, 2013, vol. 135(17), 6415-6418.
Siskin, et al., "Aqueous Organic Chemistry. 5. Diaryl Ethers: Diphenyl Ether, 1-phenoxynaphthalene and 9-phenoxyphenanthrene," Fuel, 1993, vol. 72(10), 1435-1444.

* cited by examiner

SELECTIVE C—O BOND CLEAVAGE OF OXIDIZED LIGNIN AND LIGNIN-TYPE MATERIALS INTO SIMPLE AROMATIC COMPOUNDS

BACKGROUND

Due to the depletion of petroleum-based fuels and chemicals and their detrimental impact on the environment, a transition to renewable fuels and chemicals is garnering considerable attention. ((a) U.S. Energy Information Administration/Annual *Energy Review* 2011, Washington, D.C. 20585. (b) Corma, A.; Iborra, S.; Velty, A. *Chem. Rev.* 2007, 107, 2411. (c) Chheda, J. N.; Huber, G. W.; Dumesic, J. A. *Angew. Chem.* 2007, 119, 7298; *Angew. Chem. Int. Ed.* 2007, 46, 7164.) Of these renewable sources, lignocellulosic biomass (cellulose, hemicellulose, and lignin) plays a crucial role. Lignin is a major component of non-edible biomass (15-30% by weight; 40% by energy). ((a) Zakzeski, J.; Bruijnincx, P. C. A.; Jongerius, A. L.; Wechhuysen, B. M. *Chem, Rev.* 2010, 110, 3552. (b) Ralph, J., Encyclopedia of Life Sciences, Lignins, © 2007 John Wiley & Sons, Ltd.)

Lignin is also a cheap byproduct in the production of pulp and biofuel. It is one of the few naturally occurring sources of high-volume aromatics and therefore represents a potentially valuable feedstock for the production of organic chemicals. ((a) Collinson, S. R.; Thielemans, W. *Coord. Chem. Rev.* 2010, 254, 1854. (b) Grabber, J. H. *Crop Sci.* 2005, 45, 820.) While conversion of cellulose and hemicellulose into pulp and ultimately fuel has been extensively studied ((a) Philippidis, G. P.; Smith, T. K.; Wyman, C. E. *Biotechnol. Bioeng.* 1993, 41, 846. (b) Kumar, P.; Barrett, D. M.; Delwiche, M. J.; Stroeve, P. *Ind. Eng. Chem. Res.* 2009, 48, 3713), lignin is generally regarded as a byproduct. It is most typically burned to harness its thermal energy in any number of processes. (Gosselink, R. J. A.; Jong, E. de; Guran, B.; Abaecherli, A. *Ind. Crops Prod.* 2004, 20, 121.)

Beyond simple combustion, there are two basic approaches to lignin utilization in common use today. (Sarkanen, K. V.; Ludwig, C. H. Lignins, Occurrence, Formation, Structure and Reactions; WileyInterscience, New York, 1971.) The first approach is to exploit the properties of this natural polymer in carbon fibers, adhesives, concrete products, oil well drilling muds, as partial phenol replacements in phenol-formaldehyde resins, and in electronic circuit boards. The second approach is to convert the lignin polymer into simple low-molecular-weight organic chemicals. Processes for oxidation of lignin and associated model compounds have been the focus of extensive investigation. ((a) Cui, F.; Wijesekera, T.; Dolphin, D. *J. Biotechnol.* 1993, 30, 15. (b) Cui, F.; Dolphin, D. *Bioorg. Med. Chem.* 1995, 3, 471. (c) Herrmann, W. A.; Weskamp, T.; Zoller, J. P.; Fischer, R. W. *J. Mol. Catal. A: Chem.* 2000, 153, 49. (d) Crestini, C.; Caponi, M. C.; Argyropoulos, D. S.; Saladino, R. *Biorg. Med. Chem.* 2006, 14, 5292. (e) Partenheimer, W. *Adv. Synth. Catal.* 2009, 351, 456. (f) Zhang, J.; Deng, H.; Lin, L. *Molecules* 2009, 14, 2747.)

For instance, the world's supply of artificial vanillin is commercially produced by oxidation of lignosulfonate from spent sulfite liquor from essentially a single mill. (Hocking, M. B.; *J. Chem. Educ.* 1997, 74, 1059.) The process is via fairly simple oxidation, using molecular oxygen or stoichiometric CuO in aqueous basic solution. ((a) Larsson, S.; Miksche, G. E. *Acta. Chem. Scand.* 1971, 25, 647. (b) Pepper, J. M. Casselma, B. W.; Karapall, J. C. *Can. J. Chem.* 1967, 45, 3009.) The process, however, uses a lignosulfonate feedstock that arises from the expensive and more polluting sulfite pulping process, which is used in very few mills today. Also, oxidation of lignin with stoichiometric nitrobenzene in 1M NaOH at 170° C. to produce vanillin and syringaldehyde (up to ~20%) is known. ((a) Yamamura, M.; Hattori, T.; Suzuki, D. S. *Plant Biotech.* 2010, 27, 305. (b) Nillar, J. C.; Caperos, A.; GarciaOchoa, F. J. *Wood Chem. Technol.* 1997, 17, 259.)) (See Scheme 1 for the structure of vanillin and syringaldehyde). This process, however, is not suitable for industrial use because of its high energy; thus it is not scalable. (The reaction can be explosive, even at laboratory scale.)

Scheme 1. Simple aromatic chemicals derived from lignin oxidation.

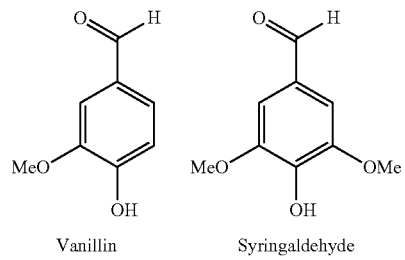

Vanillin           Syringaldehyde

All of these methods suffer from environmental concerns, safety concerns and lack of structural specificity when starting from raw lignin. Therefore, identifying new chemical transformations of lignin that can proceed with high efficiency and selectivity is a long-felt and unmet need.

Lignin is a highly complex biopolymer having a variable structure. The variability of lignin's structure depends, at least in part, on its origin. The most common structural feature in all lignins is a β-O-4 linkage between aromatic rings (>85%; see Scheme 2). ((a) Ibrahim, W.; Lundquist, K. *Acta. Chem. Scand.* 1994, 48, 149. (b) Martínz, Á. T.; Rencoret, J.; Marques, G.; Gutiérrez, A.; Ibarra, D.; Jimenez-Barbero, J.; del Rio, J. C. *Phytochemistry* 2008, 69, 2831. (c) Vanholme, R.; Demedts, B.; Morreel, K.; Ralph, J.; Boerjan, W. *Plant Physiology,* 2010, 153, 895.) Another structural feature of lignin is aromatic rings containing secondary benzylic alcohol substituents and primary aliphatic alcohol substituents. Simple model compounds, such as 1, have been used to simulate the chemical reactivity expected from authentic samples of lignin.

Scheme 2. Representative sturcture of lignin and the corresponding β-O-4-linked model compound 1.

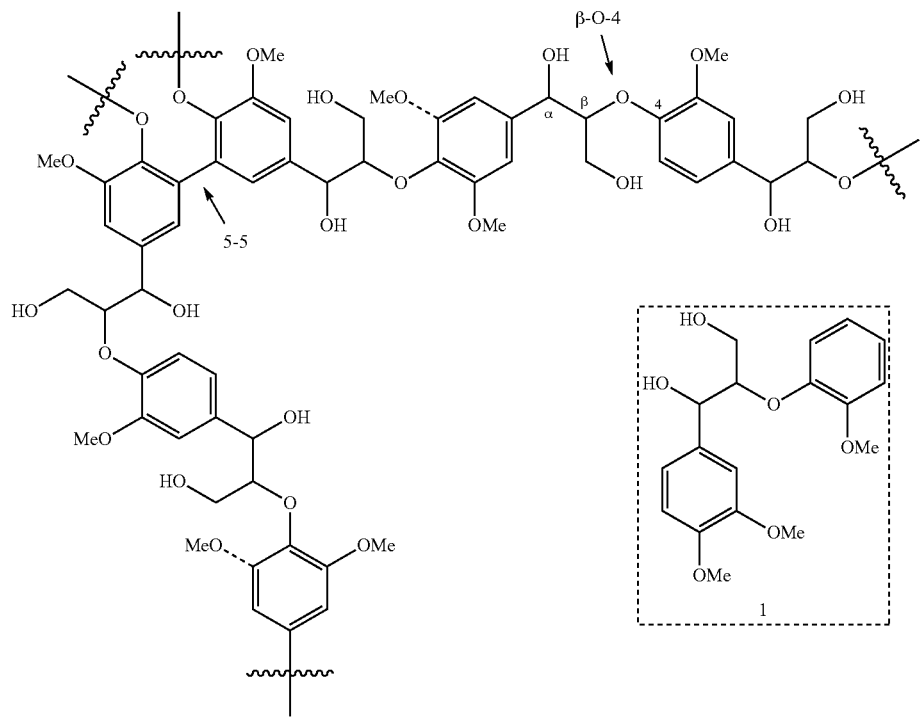

Recent studies have begun to make progress in the development of catalytic aerobic oxidation of more realistic lignin model compounds, such as 1. For example, some research groups have identified several vanadium complexes that show promising aerobic reactivity, in several cases promoting multistep reactions that directly afford C—C/C—O cleavage products. ((a) Son, S.; Toste, D. *Angew. Chem. Int. Ed.* 2010, 49, 3791. (b) Hanson, S. K.; Baker, R. T.; Gordon, J. C.; Scott, B. L.; Thorn, D. L. *Inorg. Chem.* 2010, 49, 5611. (c) Hanson, S. K.; Wu, R.; Silks, L. A. *Angew. Chem. Int. Ed.* 2012, 51, 3410. (d) Zhang, G.; Scott, B. L.; Wu, R.; Silks, L. A.; Hanson, S. A. *Inorg. Chem.* 2012, 51, 7354.)

The irregular and complex structure of lignin, along with unsustainable approaches in the art, present profound technical, economic, and environmental challenges to using lignin and lignin-like materials as a bio-based chemical feedstock. Chemoselective depolymerization of lignin materials to value-added chemicals is a key step in this process. As discussed above, a number of homogenous and heterogeneous catalyst systems have been examined. However, all of these approaches suffer from insurmountable problems, such as non-selective transformations (which results in widely variable product mixtures), a huge array of low-yield products (thus making product separation difficult and/or impossible, as well as cost-prohibitive), prohibitive catalyst prices, and production of large quantities of unwanted, low-value by-products. Thus, there remains a long-felt and unmet need for a method to depolymerize lignin and lignin-like materials selectively, without the need for precious metal catalysts, and without requiring harmful, explosive, or otherwise difficult-to-handle reagents.

SUMMARY OF THE INVENTION

Disclosed is a method to depolymerize lignin or lignin sub-units. The method comprises oxidizing at least a portion of secondary benzylic alcohol groups and/or a portion of primary alcohol groups in the lignin or lignin sub-unit to corresponding ketones, and then selectively cleaving C—O bonds and/or C—C in at least a portion of β-O-4 linkages in the lignin or lignin sub-unit, thereby yielding low molecular-weight aromatic compounds. See, for Example, Scheme 3, below. Note that a β-O-4 linkage includes two bonds aliphatic bonds: the C—C bond between the α-position carbon atom and the β-position carbon atom, and a C—O bond between the β-position carbon atom and the ether oxygen atom. Oxidizing the secondary benzylic alcohol groups and/or the primary alcohol groups in the lignin or lignin sub-unit may be accomplished by any means now known or developed in the future. The C—O or C—C bonds in the oxidized lignin or lignin sub-unit are cleaved by reacting it with a reagent comprising an organic carboxylic acid and/or a salt of an organic carboxylic acid, and/or an ester of an organic carboxylic acid. The preferred reagent for the cleavage step is formic acid and/or a formic acid salt.

Specifically disclosed herein is a method to cleave C—C and C—O bonds in β-O-4 linkages in lignin or lignin sub-units. The method comprises oxidizing at least a portion of secondary benzylic alcohol groups in β-O-4 linkages in the lignin or lignin sub-unit to corresponding ketones. This intermediate is referred to herein as an oxidized lignin or lignin sub-unit. Then the C—O or C—C bonds in the oxidized lignin or lignin sub-unit are cleaved by reacting it with an an organic carboxylic acid, and/or a salt of an organic carboxylic acid, and/or an ester of an organic carboxylic acid, for a time and a temperature at which at least a portion of β-O-4 linkages in the oxidized lignin or lignin sub-unit are cleaved.

The second step of the method, i.e., the cleavage step, may be conducted in the presence or absence of a metal. If a metal is used, it is preferred, although not required, that the metal be selected from Groups 3 to 12 of the periodic table of elements.

(That it, those metals colloquially referred to as "transition metals.") The metal may be present in stoichiometric concentration or above or below stoichiometric concentration.

The method in full may be conducted at any suitable temperature. However, the cleavage step is preferably conducted at a temperature of from about 75° C. to about 300° C., or from about 75° C. to about 150° C., or from about 100° C. to about 150° C. The cleavage step may also be conducted at any suitable pressure. The preferred pressure is range for the cleavage step is from about atmospheric to about 300 psi, or from about atmospheric to about 200 psi, or from about atmospheric to about 100 psi.

The oxidation of the lignin or lignin sub-unit may be accomplished by contacting the lignin or lignin sub-unit with a catalyst comprising nitric acid ($HNO_3$) in combination with another Brønsted acid, in the absence of a metal-containing catalyst, thereby yielding the oxidized lignin or lignin sub-unit. The initial oxidation step is preferably conducted in a polar aprotic solvent containing from 0% up to about 20 wt % water. The Brønsted acid may optionally be selected from the group consisting of hydrochloric acid (HCl), hydrobromic acid (HBr), hydrofluoric acid (HF), hydroiodic acid (HI), phosphoric acid ($H_3PO_4$), sulfuric acid ($H_2SO_4$), boric acid ($B(OH)_3$), tetrafluoroboric acid ($HBF_4$), perchloric acid ($HClO_4$), acetic acid ($CH_3C(O)$—OH), trifluoroacetic acid ($CF_3C(O)$—OH), methanesulfonic acid ($CH_3SO_3H$), solid acid resins containing sulfonic acid sites, and solid acid resins containing benzoic acid sites.

The lignin or lignin sub-unit may be selectively oxidized by contacting the lignin or lignin sub-unit with a catalyst comprising nitric acid ($HNO_3$) in combination with another Brønsted acid, in the absence of a metal-containing catalyst, thereby yielding a selectively oxidized lignin or lignin sub-unit.

The method may be carried out in any suitable solvent. Polar aprotic solvent are preferred. The preferred solvent is a nitrile, most preferably acetonitrile. The solvent may also contain up to 20 wt % water, preferably from about 2 wt % to about 15 wt % water, and more preferably from about 2 to about 10 wt % water.

In the preferred version of the method, the catalyst comprises $HNO_3$ in combination with a Brønsted acid selected from the group consisting of hydrochloric acid (HCl), hydrobromic acid (HBr), hydrofluoric acid (HF), hydroiodic acid (HI), phosphoric acid ($H_3PO_4$), sulfuric acid ($H_2SO_4$), boric acid ($B(OH)_3$), tetrafluoroboric acid ($HBF_4$), perchloric acid ($HClO_4$), acetic acid ($CH_3C(O)$—OH), trifluoroacetic acid ($CF_3C(O)$—OH), methanesulfonic acid ($CH_3SO_3H$), solid acid resins containing sulfonic acid sites, and solid acid resins containing benzoic acid sites. The preferred combination comprises, consists essentially of, or consists of $HNO_3$ and HCl. It is generally preferred, although not required, that the $HNO_3$ and the Brønsted acid are each present in a concentration of from about 2 mol % to about 20 mol %.

The selective oxidation may be conducted in contact with atmospheric air or the selective oxidation may conducted in an environment comprising an $O_2$ partial pressure of at least about 1 atm.

The selective oxidation reaction disclosed herein may be conducted at a temperature of from about 10° C. to about 100° C., or from about 20° C. to about 80° C., or from about 25° C. to about 50° C.

The selective oxidation reaction may be conducted in the absence of a nitroxyl radical. Alternatively, the selective oxidation reaction may be conducted in the presence of a reagent comprising a nitroxyl radical. If a nitroxyl radical is present, it is preferred, but not required, that it is selected from the group consisting of TEMPO, NHAc-TEMPO, 4-$C_{1-6}$-alkyloxy-TEMPO, 4-hydroxy-TEMPO, diphenylnitroxyl, di-tert-butylnitroxyl, 9-azabicyclo[3.3.1]nonane N-oxyl (ABNO), and AZADO. The nitroxyl radical may be present in a concentration of from about 2 mol % to about 10 mol %.

In one specific version of the process, the reaction comprises contacting the lignin or lignin sub-unit with a catalyst comprising $HNO_3$ and HCl, in a solvent system comprising acetonitrile and water, and the reaction is conducted in the presence of a reagent selected from the group consisting of TEMPO, NHAc-TEMPO, 4-$C_{1-6}$-alkyloxy-TEMPO, 4-hydroxy-TEMPO, diphenylnitroxyl, di-tert-butylnitroxyl, 9-azabicyclo[3.3.1]nonane N-oxyl (ABNO), and AZADO. In this specific version of the process, the $HNO_3$ and HCl may present in a concentration of from about 5 mol % to about 15 mol %. Concentrations above and below these levels are within the scope of the claims. The selective oxidation reaction may be conducted in contact with atmospheric air, or in an environment comprising an $O_2$ partial pressure of at least about 1 atm. The preferred temperature ranges are as stated previously.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in organic chemistry.

DETAILED DESCRIPTION

Figure 1:
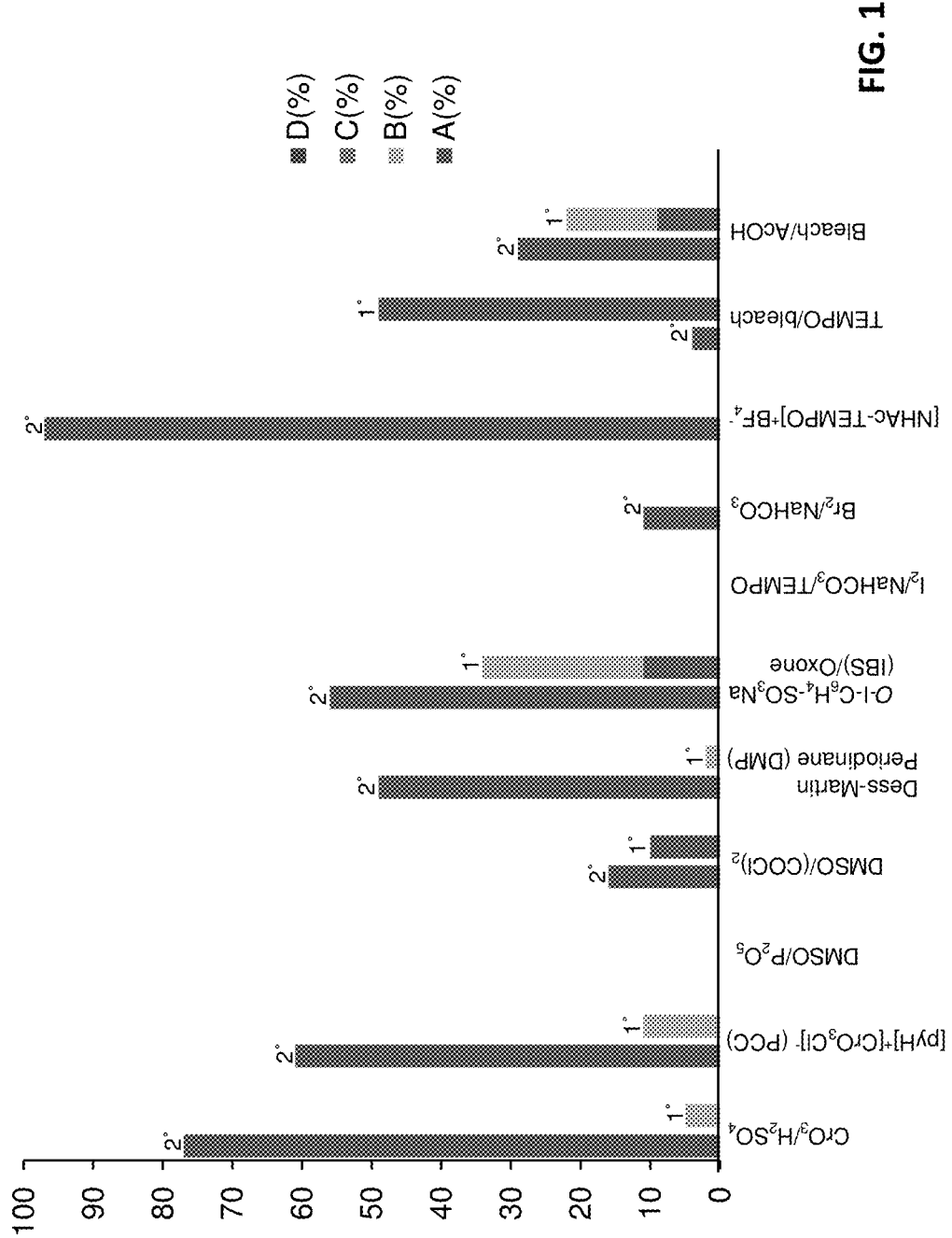
FIG. 1 is a histogram depicting products derived from oxidation of primary and secondary alcohols in lignin model compounds.

Abbreviations and Definitions:

NHAc-TEMPO=AA-TEMPO=4-Acetamido-(2,2,6,6-tetramethylpiperidin-1-yl)oxyl:

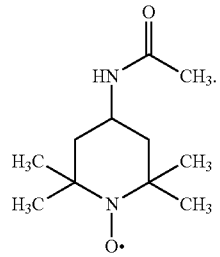

(CAS Number 14691-89-5. Commercially available from Sigma-Aldrich, St. Louis, Mo., USA; catalog no. 390380).

AZADO=2-Azaadamantane-N-oxyl (CAS No. 57625-08-8; Sigma-Aldrich catalog no. 701718):

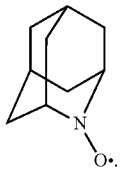

Brønsted acid, Brønsted base: As used herein, a Brønsted acid is a molecule or ion that is able to lose, or "donate," a hydrogen cation (proton, H⁺). A Brønsted base is a molecule or ion with the ability to gain, or "accept," a hydrogen cation. The term "Brønsted acid" explicitly includes, but is not limited to, hydrochloric acid (HCl), hydrofluoric acid (HF), hydrobromic acid (HBr), hydroiodic acid (HI), phosphoric acid ($H_3PO_4$), sulfuric acid ($H_2SO_4$), boric acid ($B(OH)_3$), tetrafluoroboric acid ($HBF_4$), perchloric acid ($HClO_4$), acetic acid ($CH_3C(O)$—OH), trifluoroacetic acid ($CF_3C(O)$—OH), methanesulfonic acid ($CH_3SO_3H$), solid acid resins containing sulfonic acid sites, and solid acid resins containing benzoic acid sites bpy=2,2'-bipyridine (CAS No. 366-18-7; Sigma-Aldrich catalog no. 14453):

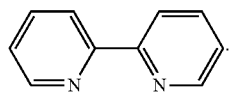

2,9-dimethyl-1,10-phenanthroline (also known as neocuproine; CAS No. 484-11-7; Sigma-Aldrich catalog no. N1501):

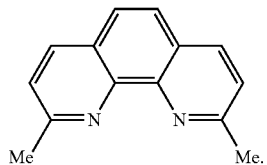 [SMILES: Cc1ccc2ccc3ccc(C)nc3c2n1]

DCE=dichloroethane.

DMSO=dimethylsulfoxide.

HRMS (EI)=high-resolution mass spectrometry-electrospray ionization.

MeCN=acetonitrile.

Nitroxyl radical=A molecule of formula R—NO•. Nitroxyl radicals include, but are not limited to, TEMPO, NHAc-TEMPO, 4-$C_{1-6}$-alkyloxy-TEMPO, 4-hydroxy-TEMPO, diphenylnitroxyl, di-tert-butylnitroxyl, 9-azabicyclo[3.3.1]nonane N-oxyl (ABNO), and AZADO.

NMI=N-methylimidazole (synonymous with 1-methylimidazole; CAS No. 616-47-7; Sigma-Aldrich catalog no. M50834):

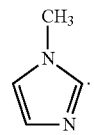

Organic carboxylic acid: As used herein, the term "organic carboxylic acid" refers to any organic acid having at least one carboxylic acid group. Organic carboxylic acids have the general structure R—C(=O)—OH, where "R" is typically alkyl, alkenyl, alkynyl (linear, branched, cyclic), aryl, etc., which may be optionally substituted, for example, with halo. "R" may also include one or more additional carboxylic acid sites. Thus, a non-limiting list of organic carboxylic acids includes, but is not limited to, formic acid, acetic acid, propionic acid, mono-, di-, and tri-halo acetic acids, oxalic acid, maleic acid, succinic acid, benzoic acid, and the like. As is well known in the art, a salt of an organic carboxylic acid comprises the deprotonated carboxylic acid and an associated counterion, such as Group 1 and 2 metal ions (e.g., lithium, sodium, potassium, calcium, magnesium, etc.). Salts of organic carboxylic acids have the general formula R—C(=O)—O⁻[M]⁺, where "M" is a metallic counterion. Similarly, an ester of an organic carboxylic acid is formed by reacting the carboxylic acid with a hydroxyl-containing group, usually an alcohol. An ester of an organic carboxylic acid thus has the general formula R—C(=O)—O—R', where R and R' are as described above for R.

Polar aprotic solvent: As used herein, the term "polar aprotic solvent" explicitly includes, but is not limited to tetrahydrofuran (THF), ethyl acetate (EtOAc), acetone, dimethylformamide (DMF), hexamethylphosphoramide (HMPA), acetonitrile (MeCN), and dimethyl sulfoxide (DMSO).

TEMPO=(2,2,6,6-Tetramethylpiperidin-1-yl)oxyl (CAS Number 2564-83-Sigma-Aldrich catalog no. 2214000):

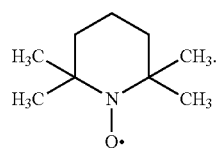

General Approach:

Model compound 1 includes two different types of hydroxyl functional groups: a primary alcohol group, as well as a secondary benzylic alcohol group. The oxidation of 1 with both traditional chemical oxidants and metal-catalyzed aerobic oxidations methods was investigated to obtain a range of oxidation products and also to establish the intrinsic reactivity patterns of the lignin-like model compound under a variety of oxidizing conditions.

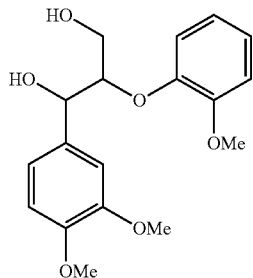

1

In the present process, the proposed reaction strategies for selectively deconstructing lignin are depicted in Scheme 3. As shown in Scheme. 3, pathway I depicts the products expected if the primary alcohol group is selectively oxidized to the corresponding aldehyde.

Pathway II depicts the products expected if the secondary benzylic alcohol group is selectively oxidized to the corresponding ketone. Selective cleavage of the aliphatic carbon-carbon bond linking the two aromatic moieties in the oxidized intermediates yields the products shown on the right of Scheme 3.

In the present approach, the reaction of model compound 1 with FFvarious traditional oxidants was investigated in an attempt to selectively oxidize the secondary benzylic alcohol group. The possible reactions are depicted in Scheme 4. The various possible products are designated alphabetically as compounds A, B, C, and D. Results of the experiments are depicted in FIG. 1. Good-to-excellent yields and selectivities for oxidation of the secondary benzylic alcohol were observed with $Cr^{VI}$-oxide, Dess-Martin periodinane and TEMPO-oxoammonium reagents. Veratryl aldehyde (D), observed as a minor product in several of these reactions, is believed to arise from oxidation of the primary alcohol followed by retro-aldol addition. (Tarabanko, V. E.; Fomova, N. A.; Kuznetsov, B. N.; Ivanchenko, N. M.; Kudryashev, A. V. *React. Kinet. Catal. Lett.* 1995, 55, 161.) Activated DMSO methods (e.g., Swern; FIG. 1, entry 3) and stoichiometric TEMPO in AcOH exhibited poor selectivity, affording products derived from both primary and secondary alcohol oxidation. Bleach in combination with catalytic TEMPO (2 mol %) at pH 9 was the only reagent to exhibit good selectivity for primary alcohol oxidation.

Scheme 3. Chemoselective alcohol oxidation strategies for lignin/lignin model compounds.

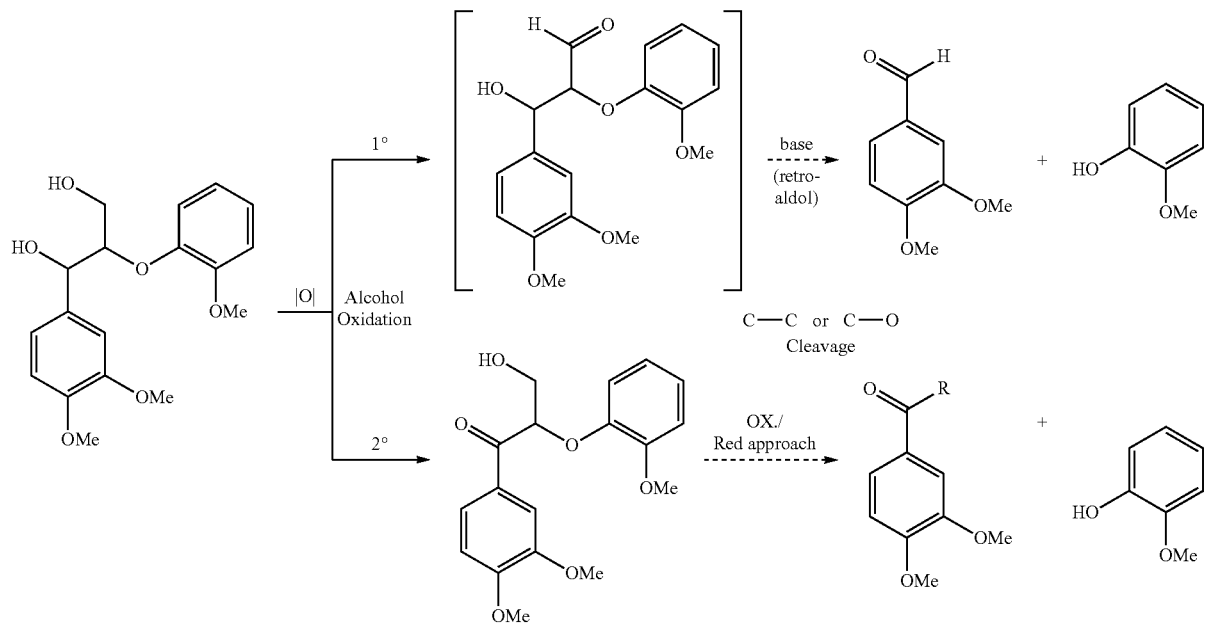

Scheme 4. Chemoselective oxidation of primary and secondary alcohol groups in model compound 1.

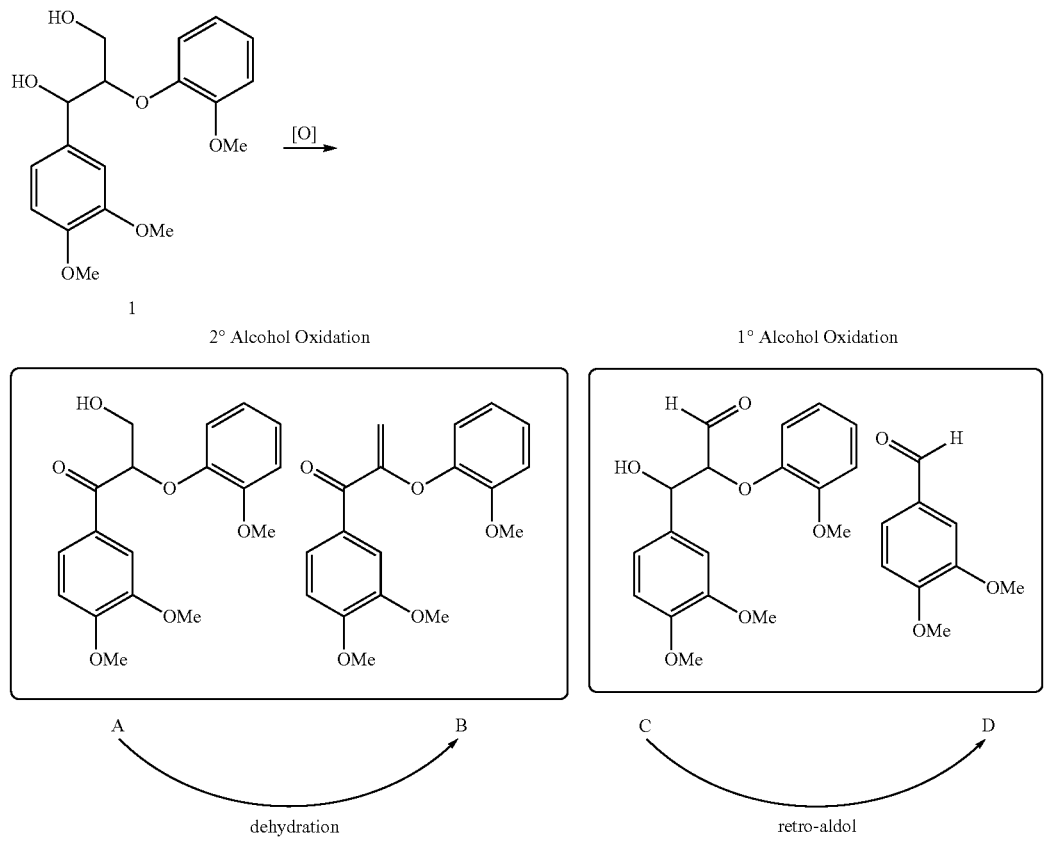

These results established useful benchmarks for developing analogous metal-catalyzed oxidation methods that use $O_2$ as the stoichiometric oxidant. A number of reported aerobic alcohol oxidation catalyst systems were then tested. The conventional methods afford low conversion and/or low selectivity in the oxidation of the dimeric model compound 1 (See Table 1). As shown in Table 1, the catalytic oxidation of model compounds 1 with Cu(I) and Cu(II) salts with TEMPO derivatives (Table 1, entries 1-8) in acetonitrile resulted in the formation of products derived from both secondary benzylic alcohol oxidation and primary aliphatic alcohol oxidation. Attempts to perform the aerobic oxidation of 1 with $Pd(OAc)_2$ in DMSO (Table 1, entry 9) led to 44% conversion and high selectivity (42% of compound A as the only product) in 15 h. ((a) Steinhoff, B. A.; Fix, S. R.; Stahl, S. S. *J. Am. Chem. Soc.* 2002, 124, 766. (b) Steinhoff, B. A.; Stahl, S. S. *J. Am. Chem. Soc.* 2006, 128, 4348.) Conducting the reaction in a mixture of DMSO and water (Table 1, entry 10) and also utilizing 2,9-dimethyl-1,10-phenanthroline as a ligand for $Pd(OAc)_2$, gave 87% conversion with high selectivity (56% of compound A as the only product). (Brink, G. J.; Arends, I. W. C. E.; Hoogenraad, M.; Verspui, G.; Sheldon, R. A. *Adv. Synth. Catal.* 2003, 345, 1341.) Moreover, a full conversion of this substrate has been achieved with good selectivity (approx. 40:1; 79% yield of compound

TABLE 1

Products derived from metal-catalyzed aerobic oxidation of model compound 1.

| entry[a] | metal salts (mol %) | ligand (mol %) | additives 1 | additives 2 | additives 3 | solvent | time (h) | conversion (%)[b] | Yield (%)[b] A | B | C | D | E |
|---|---|---|---|---|---|---|---|---|---|---|---|---|---|
| 1 | Cu(OTf)(MeCN)$_4$ (10) | bpy (10) | TEMPO (10 mol %) | — | — | MeCN | 24 | 77 | 9 | 0 | 2 | 25 | 13 |
| 2 | Cu(OTf)(MeCN)$_4$ (10) | bpy (10) | TEMPO (10 mol %) | NMI (20 mol %) | — | MeCN | 24 | 56 | 0 | 0 | 1 | 30 | 9 |
| 3 | CuBr (10) | bpy (10) | 4-OMe-TEMPO (10 mol %) | — | — | MeCN | 24 | 78 | 2 | 26 | 2 | 30 | 13 |

TABLE 1-continued

Products derived from metal-catalyzed aerobic oxidation of model compound 1.

| entry[a] | metal salts (mol %) | ligand (mol %) | additives 1 | additives 2 | additives 3 | solvent | time (h) | conversion (%)[b] | Yield (%)[b] A | B | C | D | E |
|---|---|---|---|---|---|---|---|---|---|---|---|---|---|
| 4 | CuBr (10) | bpy (10) | TEMPO (10 mol %) | DABCO (10 mol %) | — | MeCN | 24 | 86 | 6 | 23 | 3 | 31 | 11 |
| 5 | CuBr (10) | bpy (10) | TEMPO (10 mol %) | — | — | MeCN | 24 | 89 | 10 | 0 | 0 | 37 | 14 |
| 6 | CuI (10) | bpy (10) | — | — | — | MeCN | 20 | 32 | 23 | 0 | 0 | 3 | 0 |
| 7 | Cu(OTf)$_2$ (5) | 4,4'-tBu$_2$-bpy (5) | TEMPO (5 mol %) | DABCO (5 mol %) | NMI (5 mol %) | MeCN | 24 | 70 | 0 | 21 | 2 | 22 | 0 |
| 8 | Cu(TFA)$_2$ (5) | 4,4'-tBu$_2$-bpy (5) | TEMPO (5 mol %) | DABCO (5 mol %) | NMI (5 mol %) | MeCN | 24 | 71 | 1 | 21 | 3 | 24 | 3 |
| 9 | Pd(OAc)$_2$ (5) | — | — | — | — | DMSO | 15 | 44 | 42 | 0 | 0 | 0 | 0 |
| 10 | Pd(OAc)$_2$ (5) | 2,9-dimethyl-1,10-phenantroline (10) | — | — | — | DMSO:H$_2$O (40:60) | 15 | 87 | 56 | 0 | 0 | 0 | 0 |
| 11 | Fe(NO$_3$)$_3$ (5) | — | TEMPO (10 mol %) | NaCl (10 mol %) | | DCE | 20 | 100 | 79 | 0 | 0 | 2 | 0 |
| 12 | Fe(NO$_3$)$_3$ (10) | salen (10) | — | — | | MeCN | 20 | 0 | 0 | 0 | 0 | 0 | 0 |
| 13 | Fe(acac)$_3$ (10) | Phen (10) | K$_2$CO$_3$ (1 equiv) | NaOH (0.5 quiv) | — | toluene | 20 | 43 | 19 | 0 | 0 | 8 | 0 |
| 14 | RuCl$_2$(PPh$_3$)$_3$ (4) | — | TEMPO (12 mol %) | — | — | Cl—C$_6$H$_5$ | 20 | 30 | 17 | 0 | 3 | 5 | 0 |

[a]All reactions run at 60° C. and 1 atm O$_2$ in 1.1 mL of solvent.
[b]Conversion and yields determined by $^1$H NMR spectroscopy versus mesitylene as internal standard and relaxation time 25 ms.

A) favoring secondary benzylic alcohol oxidation using iron(III)nitrate, TEMPO and NaCl in 1,2-dichloroethane (Ma, S.; Liu, J.; Li, S.; Chen, B.; Cheng, J. Kuang, J.; Liu, Y.; Wan, B.; Wang, Y.; Ye, J.; Yu, Q.; Yuan, W.; Yu, S. Adv. Synth. Catal. 2011, 353, 1005.) (Table 1, entry 11).

Non-Metallic Aerobic Oxidation:

The effectiveness of TEMPO-based reagents and co-catalysts in the aerobic oxidation of 1 prompted a consideration of other nitroxyl-catalyzed oxidation methods. Recently, several groups have described metal-free aerobic alcohol oxidation reactions that employ a catalytic nitroxyl species in combination with an inorganic nitrogen oxide co-catalyst. The latter species is proposed to mediate regeneration of an oxoammonium species by O$_2$. ((a) Strazzolini, P.; Runcio, A. Eur. J. Org. Chem. 2003, 2003, 526. (b) Wang, X.; Liu, R.; Jin, Y.; Liang, X. Chem. Eur. J. 2008, 14, 2679. (c) Naimi-Jamal, M. R.; Hamzeali, H.; Mokhtari, J.; Boy, J.; Kaupp, G. Chem-SusChem 2009, 2, 83. (d) Kuang, Y.; Rokubuichi, H.; Nabae, Y.; Hayakawa, T.; Kakimoto, M.-a Adv. Synth. Catal. 2010, 352, 2635. (e) Shibuya, M.; Osada, Y.; Sasano, Y.; Tomizawa, M.; Iwabuchi, Y. J. Am. Chem. Soc. 2011, 133, 6497. (f) Aellig, C.; Neuenschwander, U.; Hermans, I. ChemCatChem 2012, 4, 525. (g) Tanielyan, S. K.; Augustine, R. L.; Marin, N.; Alvez, G.; Stapley, J. Top Catal 2012, 55, 556.) A variety of TEMPO and related nitroxyl derivatives were tested as catalysts, with nitric acid or sodium nitrite as the cocatalyst. These conditions proved to be quite effective. The results are shown in Table 2. Highly selective oxidation of 1 to A was observed, with up to 95% isolated yield of A (Table 2, entry 14). The full reaction conditions associated with entry 14 featured 5 mol % AcNH-TEMPO in combination with 10 mol % HNO$_3$ and 10 mol % HCl as co-catalysts in a mixture of CH$_3$CN:H$_2$O (19:1) as the solvent (1 atm O$_2$, 45° C., 24 h).

TABLE 2

Products derived from metal-free aerobic oxidation of model compound 1 by nitroxyl radicals.

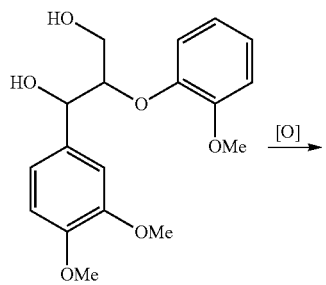

1

TABLE 2-continued

2° Alcohol Oxidation / 1° Alcohol Oxidation

Structures A, B (2° alcohol oxidation, dehydration) and C, D (1° alcohol oxidation, retro-aldol)

| entry[a] | N-nitroxyl radical (mol %) | additives (mol %) 1 | 2 | oxidant | solvent | T (°C) | time (h) | conversion (%)[a] | Yield (%)[b] A | B | C | D |
|---|---|---|---|---|---|---|---|---|---|---|---|---|
| 1 | TEMPO (4) | NaNO$_2$ (6.5) | HCl (13) | 1 atm O$_2$ | MeCN | 60 | 16 | 66 | 64 | 0 | 0 | 0 |
| 2 | NHAc-TEMPO (3.3) | NaNO$_3$ (3.3) | — | 1 atm O$_2$ | AcOH:H$_2$O (20:1) | 80 | 16 | >85 | — | — | — | — |
| 3 | NHAc-TEMPO (3.3) | HNO$_3$ (2) | — | 1 atm O$_2$ | AcOH:H$_2$O (20:1) | 80 | 16 | >85 | — | — | — | — |
| 4 | TEMPO (5) | HNO$_3$ (20) | — | air | AcOH:H$_2$O (20:1) | rt | 24 | 41 | 31 | 0 | 0 | 2 |
| 5 | NHAc-TEMPO (6.6) | HNO$_3$ (30) | — | air | AcOH:H$_2$O (20:1) | rt | 24 | 50 | 42 | 0 | 5 | 1 |
| 6 | NHAc-TEMPO (6.6) | NaNO$_2$ (100) | HNO$_3$ (10) | air | AcOH:H$_2$O (20:1) | rt | 12 | 46 | 24 | 10 | 6 | 1 |
| 7 | NHAc-TEMPO (5) | NaNO$_3$ (10) | HCl (10) | air | MeCN:H$_2$O (19:1) | rt | 24 | 9 | 8 | 0 | 0 | 0 |
| 8 | 4-OMe-TEMPO (5) | HNO$_3$ (10) | HCl (10) | 1 atm O$_2$ | MeCN:H$_2$O (19:1) | 45 | 24 | 86 | 79 | 0 | 0 | 2 |
| 9 | NHAc-TEMPO (5) | HNO$_3$ (10) | HCl (10) | 1 atm O$_2$ | AcOH:H$_2$O (19:1) | 45 | 24 | 54 | 30 | 4 | 0 | 2 |
| 10 | NHAc-TEMPO (5) | HNO$_3$ (10) | HCl (10) | 1 atm O$_2$ | EtOAc:H$_2$O (19:1) | 45 | 24 | 44 | 13 | 2 | 0 | 3 |
| 11 | NHAc-TEMPO (5) | HNO$_3$ (10) | HCl (10) | air | MeCN:H$_2$O (19:1) | rt | 24 | 74 | 68 | 0 | 0 | 0 |
| 12 | NHAc-TEMPO (5) | HNO$_3$ (10) | HBr (10) | air | MeCN:H$_2$O (19:1) | rt | 24 | 91 | 72 | 11 | 0 | 4 |
| 13 | NHAc-TEMPO (5) | HNO$_3$ (10) | HCl (10) | 1 atm O$_2$ | MeCN | 45 | 24 | 89 | 83 | 0 | 0 | 0 |
| 14 | NHAc-TEMPO (5) | HNO$_3$ (10) | HCl (10) | 1 atm O$_2$ | MeCN:H$_2$O (19:1) | 45 | 20 | 100 | 95 | 0 | 0 | 0 |
| 15 | AZADO (5) | HNO$_3$ (10) | HCl (10) | 1 atm O$_2$ | MeCN:H$_2$O (19:1) | 45 | 20 | 98 | 92 | 0 | 0 | 2 |

[a]All reactions run in 1 mL solvent.
[b]Conversion and yields determined by $^1$H NMR spectroscopy versus mesitylene as internal standard and relaxation time 25 ms.

Performing the aerobic oxidation of 1 in the presence of HBr under mild conditions (Table 2, entry 12) led to high percent conversion (91%), but slightly decreased selectivity in the product mixture (72% product A, 11% B and 4% D). The selected data in Table 2 show that good results were obtained with a number of nitroxyl-based catalysts, but the best results were obtained with 4-acetamido-TEMPO (AcNH-TEMPO) (See FIGS. 2A and 2B).

Figure 2A:
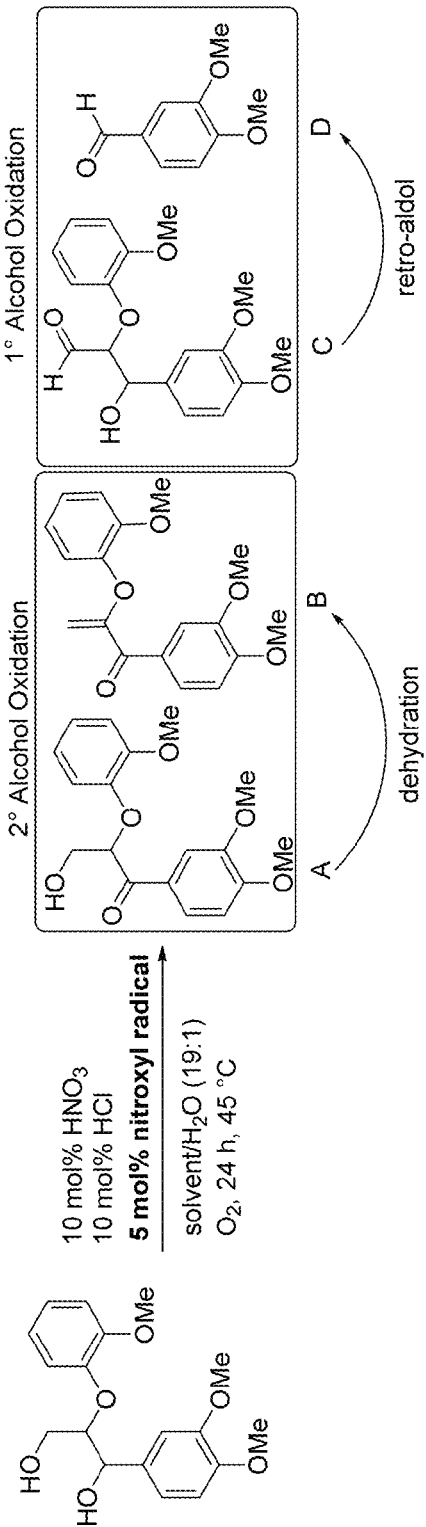
FIG. 2A is a reaction scheme depicting using a nitroxyl radical for aerobic oxidation of compound 1 with $HNO_3$/HCl.
Figure 2B:
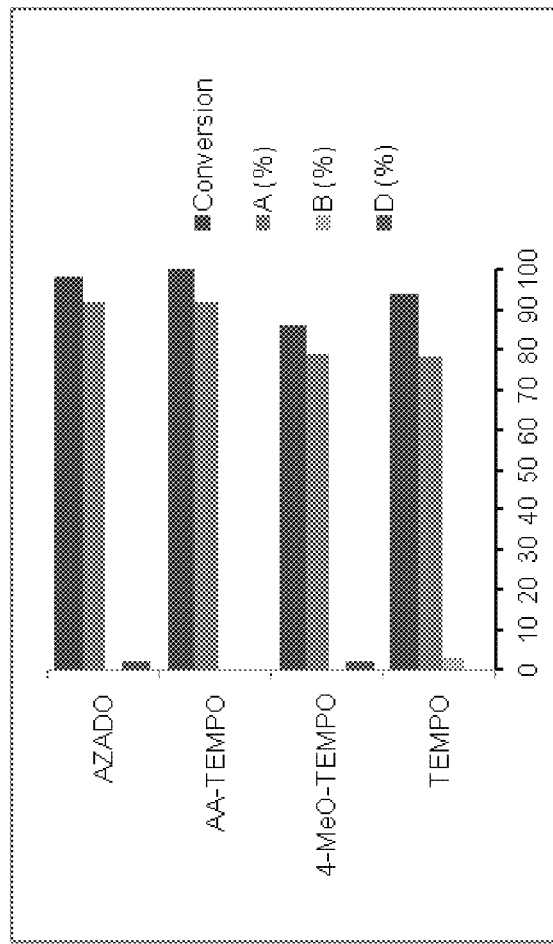
FIG. 2B is a histogram depicting the yield and conversion of the reaction shown in FIG. 5A.
Figure 3:
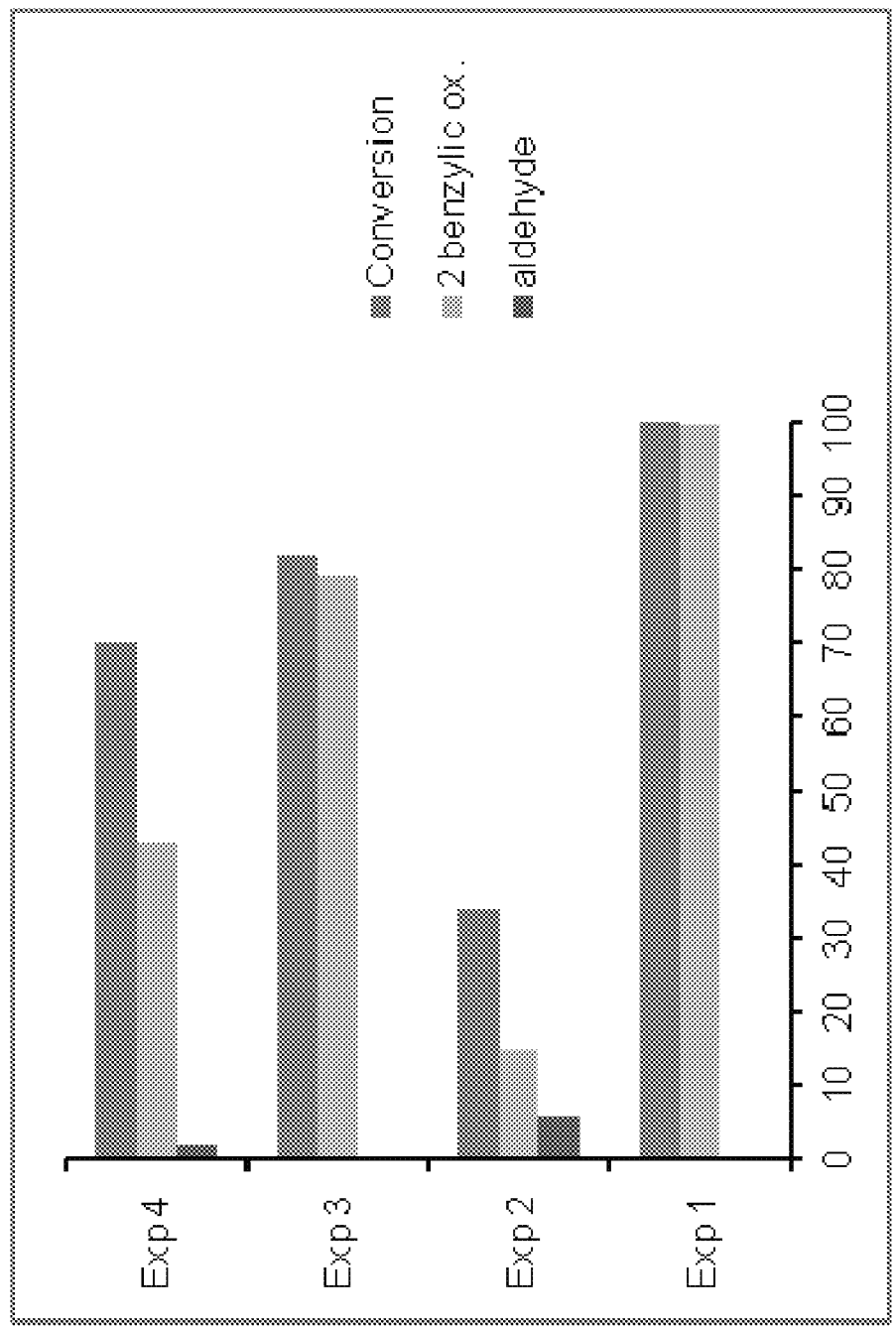
FIG. 3 is a histogram depicting yield and conversion of a metal-free, nitroxyl-free aerobic oxidation of compound 1 using $HNO_3$/HCl.

FIG. 2A depicts the reaction conditions. FIG. 2B depicts that results when utilizing different nitroxyl radicals for the aerobic oxidation of 1 with HNO$_3$/HCl. Four nixtroxyl radicals were used: AZADO, AA-TEMPO, 4-MeO-TEMPO, and TEMPO. Notably, conducting the reaction with HNO$_3$ and HCl in the absence of NHAc-TEMPO resulted in the formation of the desired product in excellent conversion and yield (See FIG. 3). FIG. 3 depicts the results of the nitroxyl-free, aerobic oxidation of 1 with HNO$_3$/HCl. In this nitroxyl-free system, inorganic nitrogen oxide plays a key role for alcohol oxidation. Keeping the nitrogen oxide gas in the reaction media requires close attention to the course of the reaction. The aerobic oxidation will lag if a substantial amount of the gas is allowed to evolve before the reaction is complete.

Using the optimized reaction conditions enables the aerobic oxidation of a variety of lignin model compounds which have been previously studied (Scheme 5).

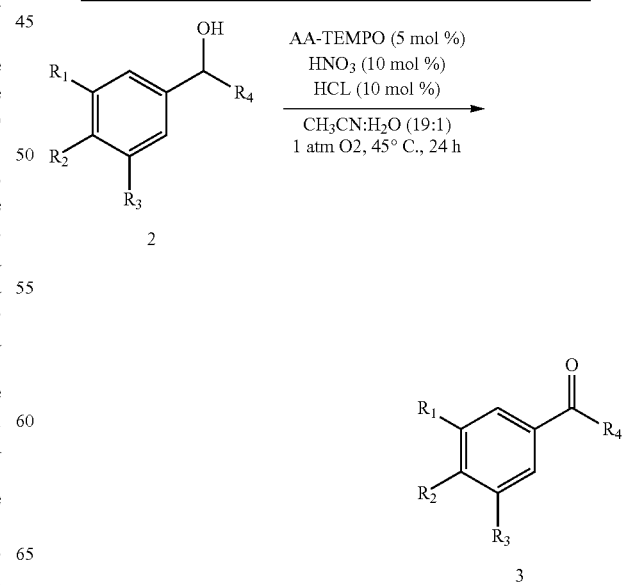

Scheme 5. Metal-free aerobic oxidation of lignin model compounds

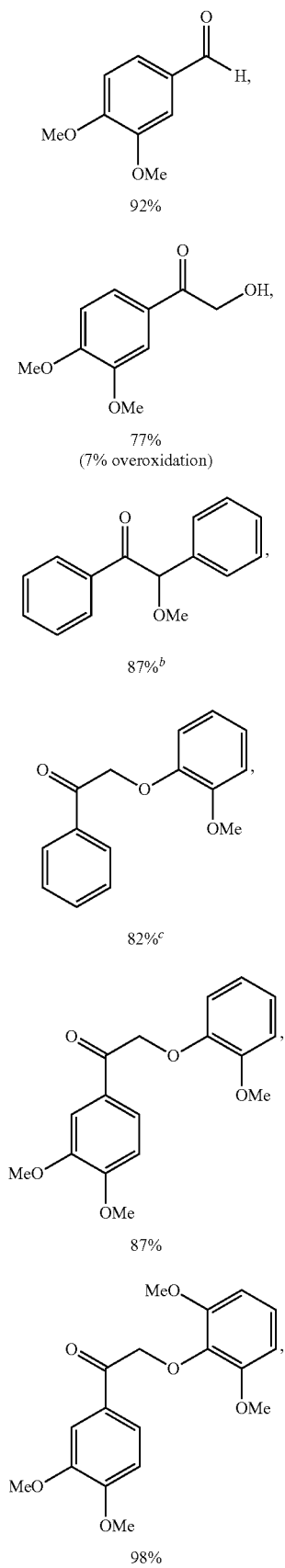
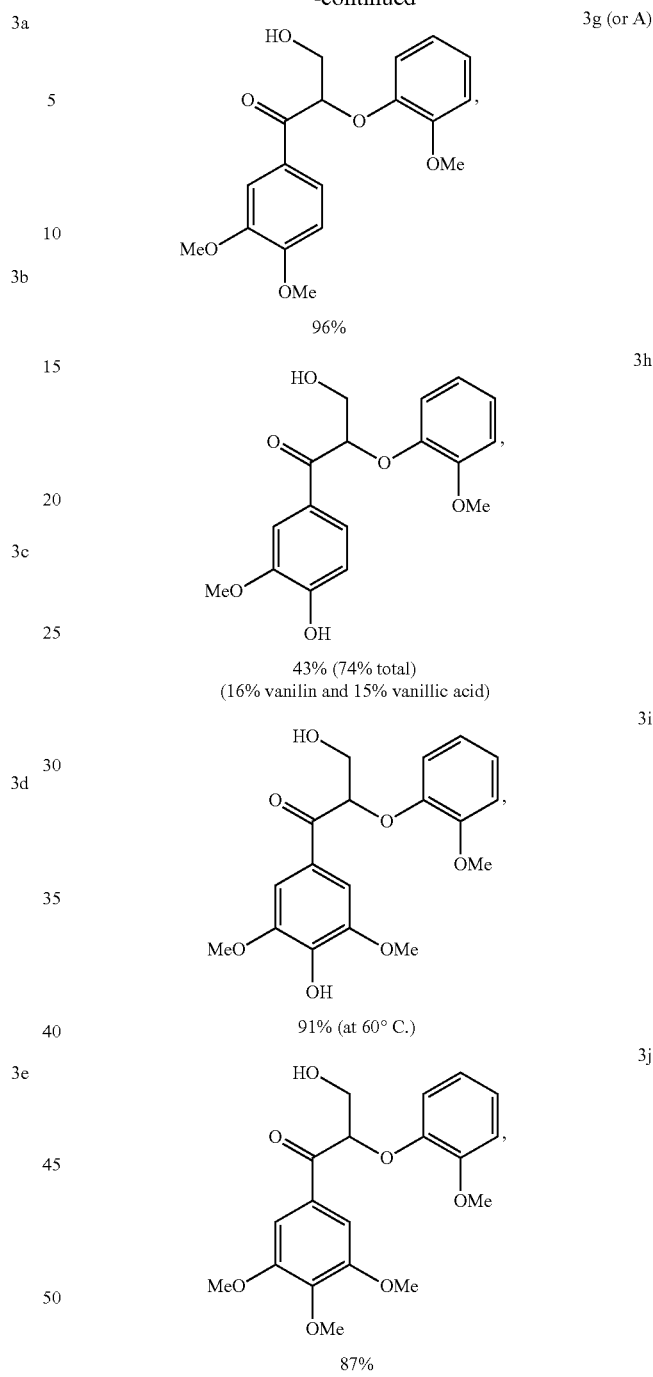

In Scheme 5, $R_1$-$R_4$ are selected independently as shown in model compounds themselves (i.e., hydrogen, hydroxyl, methoxy, or another substituted aryl group). Many of the model compounds are relatively simple benzylic alcohols (2a-2e). The AcNH-TEMPO/HNO$_3$/HCl catalyst system is quite effective in the oxidation of these compounds, affording the benzylic aldehyde or ketone (3a-3e) in 82-98% isolated yield (Scheme 5). Oxidation of the vicinal diol 2b was quite selective, affording the α-hydroxy benzylic ketone 3b in 77% yield, together with 7% of the vicinal dicarbonyl arising from oxidation of both the primary and secondary alcohols.

Despite the widespread use of compounds such 2a-f as models in lignin-conversion studies, these molecules are relatively poor chemical and structural mimics of lignin. Oxidation of the β-O-4-linked diol 1, however, remained successful under the larger scale conditions, affording a slightly better yield (96%) than obtained in the screening studies. Several additional β-O-4-linked diols were prepared and evaluated, including compounds with a trioxygenated aromatic ring (2i and 2j) similar to the syringyl (S) unit in lignin and compounds similar to the guaiacyl (G) unit in lignin (2f and 2g).

Compounds containing free phenols present unique reactivity challenges because they have been shown to decompose into complex product mixtures with other oxidation catalysts. In the present method, these types of compounds exhibited good reactivity and excellent yields of the ketone were obtained with S-type substrates 3i and 3j (87% and 91%, respectively). See Scheme 5. No C—C cleavage or overoxidation products were observed in these reactions. In contrast, oxidation of the G-type phenol 2h led to ketone 3h in 43% yield, together with a 31% yield of vanillin and vanillic acid (16% and 15% yields, respectively).

The next step in developing the process claimed herein was to develop an efficient and applicable method to cleave the aliphatic C—C bond selectively. We found exposing the pre-oxidized lignin model compound 3g (or A) to basic hydrogen peroxide (4 mL 30%) gave 71% yield of veratric acid (4). Additionally, ortho-benzoquinone and an open chain di-acid were observed as guaiacol over oxidation products (see Examples for more information). The C—C bond cleavage of cyclic 1,2-diketone with alkaline hydrogen peroxide in mixture of solvent was previously reported. Applying the modified conditions afforded complete conversion and 88% yield of veratric acid 4 at mild conditions when a mixture of solvents, THF/MeOH/H$_2$O (1:1:2), and 5 equivalents of H$_2$O$_2$ was used (Sawaki, Y.; Foote, C. S. *J. Am. Chem. Soc.* 1983, 105, 5035.) See Scheme 6. Furthermore, in this reaction 42% guaiacol 5 were also obtained.

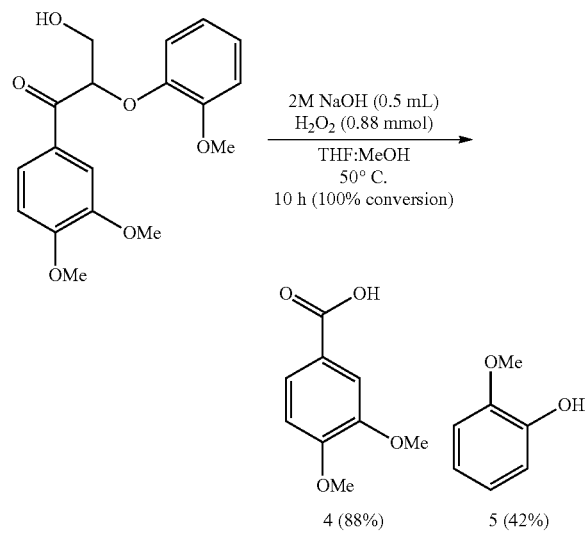

Scheme 6. Selective C—C cleavage of the pre-oxidized lignin model 3g by hydrogen peroxide.

Figure 4A:
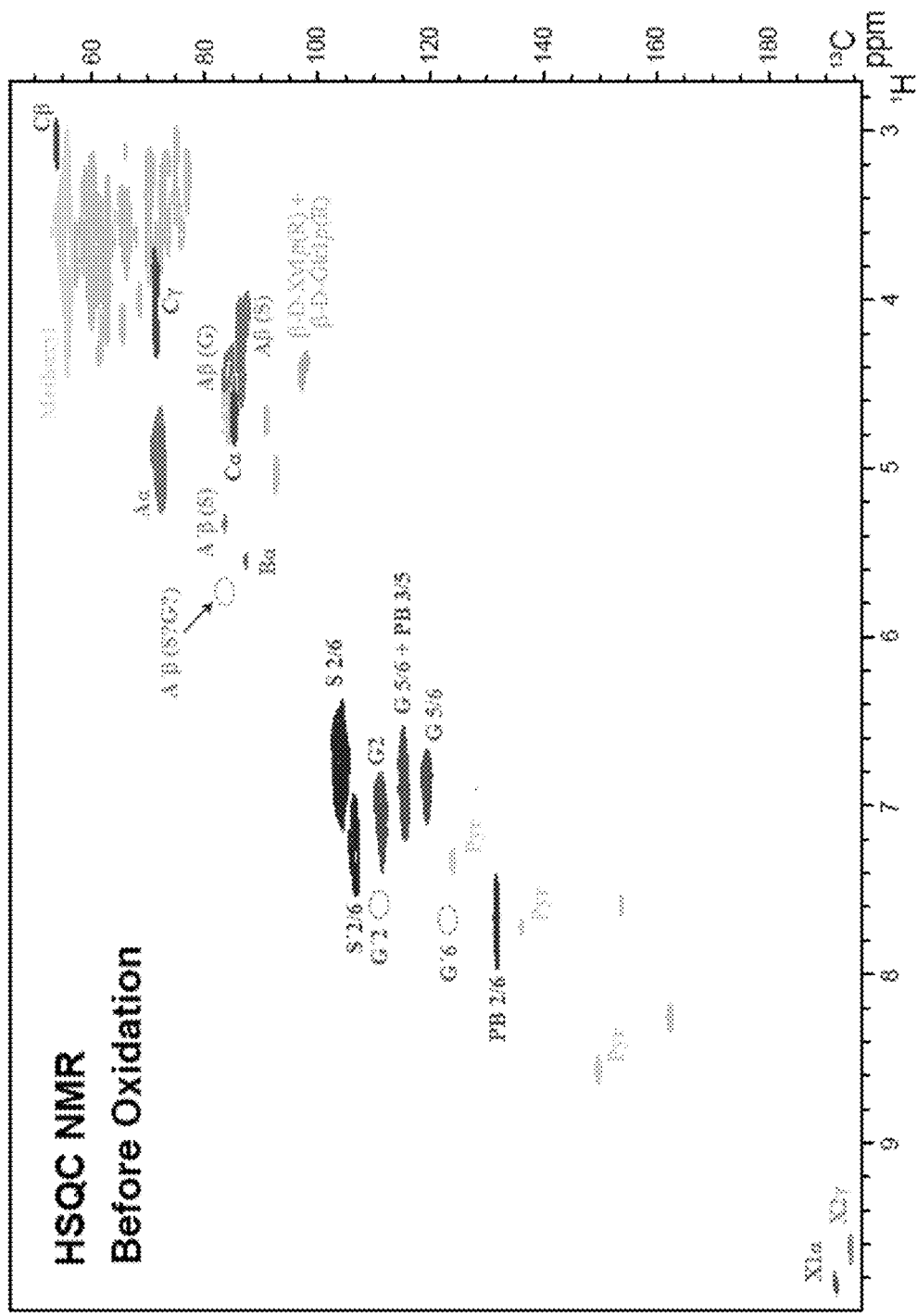
FIG. 4A is a 2-D HSQR NMR spectrum of a lignin sample before oxidation according to the present method.
Figure 4B:
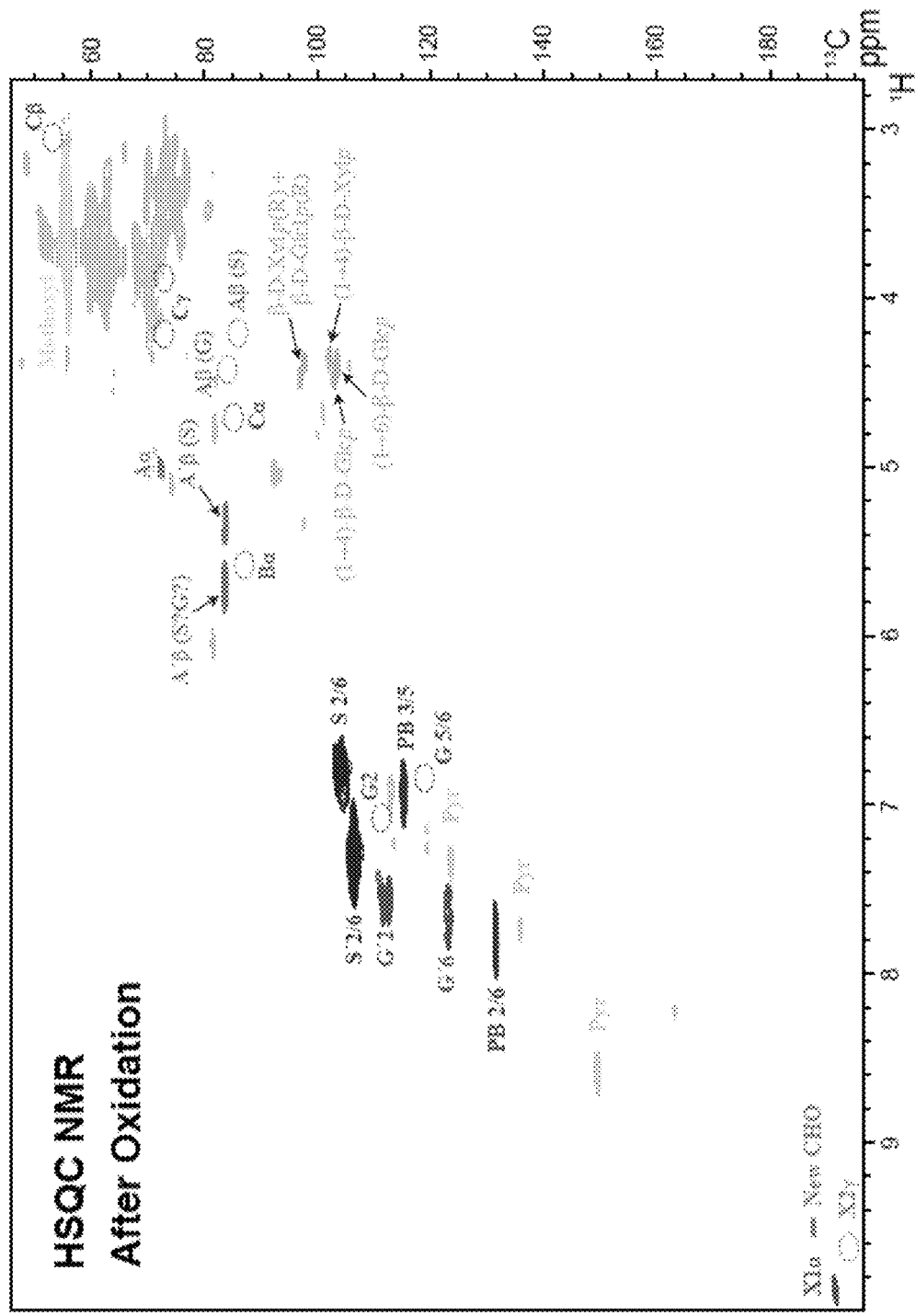
FIG. 4B is a 2-D HSQR NMR spectrum of a lignin sample after oxidation according to the present method.
Figure 4C:
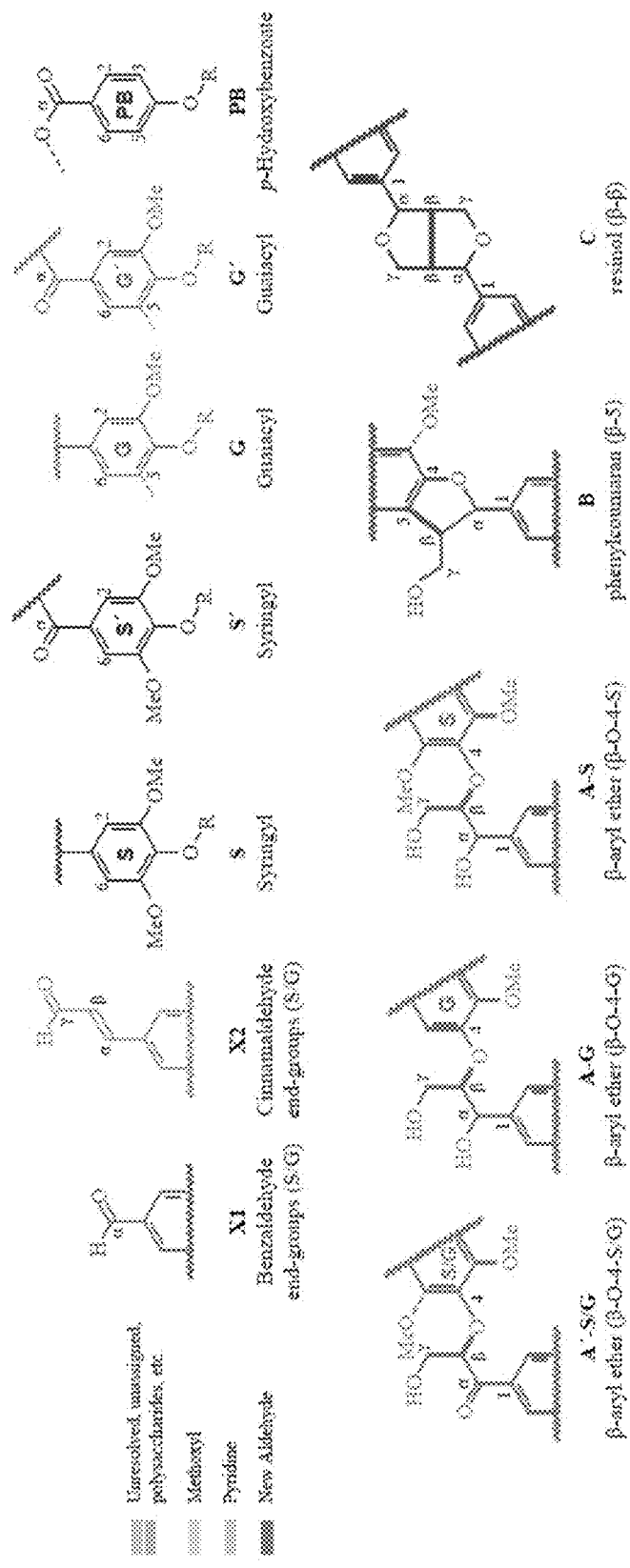
FIG. 4C is a key depicting proton assignments for the spectra shown in FIGS. 4A and 4B.

Oxidation of Authentic Aspen Lignin Sample by HNO$_3$/HCl/AA-TEMPO:

The optimized metal-free aerobic oxidation method was applied on authentic Aspen lignin sample and the resulted compound was analyzed by 2D NMR spectroscopy. The results are depicted in FIGS. 4A and 4B. FIG. 4A is the 2-D HSQR NMR spectrum of the lignin sample before oxidation. FIG. 4B is the 2-D HSQR NMR spectrum of the lignin sample after oxidation according to the present method. FIG. 4C is the key depicting proton assignments for the spectra shown in FIGS. 4A and 4B. The spectrum shows that all the secondary benzylic alcohol in guaiacyl (G) units and most part of the secondary benzylic alcohol in syringyl (S) units selectively oxidized to corresponding ketone functional groups. (Full details are provided in the Examples).

Of particular note is that the present method, in which a non-metal-containing catalyst system is used, results in the selective oxidation of benzylic secondary alcohols in both lignin model compounds and lignin itself. Also of particular note is that the system will function in both the presence and absence of the nitroxyl free-radical. This is an important economic consideration because NHAc-TEMPO, related TEMPO derivatives, and other nitroxyl radicals are relatively expensive reagents. Thus, the ability to exclude nitroxyl radicals from the catalyst system increases the economic viability of the process. Thus, the present process is the first reported metal-free aerobic method which catalyzes selective oxidation of benzylic alcohol groups in both lignin model compounds and lignin itself. See also the Examples below more information.

EXAMPLES

The Examples are provided solely to facilitate a better understanding of the process described and claimed herein. The Examples are not intended to limit the scope of the process claimed herein in any fashion.

General Considerations:

All commercially available compounds were purchased and used as received, unless otherwise noted. Solvents were dried over alumina column prior to use. Purification and drying of commercial solvents generally is not required for the catalytic reactions described in the Examples. $^1$H and $^{13}$C NMR spectra were obtained with a Varian 300 MHz, or Bruker AC-400 MHz instrumetn with the solvent peak or tetramethylsilane used as the internal reference. Multiplicities are described by using the following abbreviations: s=singlet, d=doublet, t=triplet, q=quartet, sept=septet, m=multiplet, b=broad. Flash chromatography was performed using SiliaFlash® P60 particle size 40-63 μm, 230-400 mesh. (SiliaFlash® is a registered trademark of Silicycle, Inc, Quebec City, Canada.) Some chromatography was carried out using a CombiFlash Rf® system with reusable high performance silica columns (RediSep® Rf Gold Silica, 2040 μm spherical particles). (CombiFlash Rf® and RediSep® are registered trademarks of Teledyne Instruments, Inc., Thousand Oaks, Calif., USA). Except veratryl alcohol and 2-methoxy-1,2-diphenylethanol (both from Sigma-Aldrich), the rest of the lignin model compounds were prepared according to literature procedures.

Synthesis of Lignin Model Compounds 3,4-(Dimethoxyphenyl)ethyleneglycol (2b): This compound was prepared according to a literature procedure. (Cho, D. W.; Parthasarathi, R.; Pimentel, A. S.; Maestas, G. D.; Park, H. J.; Yoon, U. C.; Dunaway Mariano, D.; Gnanakaran, S.; Langan, P.; Patrick S. Mariano, P. S. *J. Org. Chem.* 2010, 75, 6562.) Spectral data were consistent with those reported in the literature.

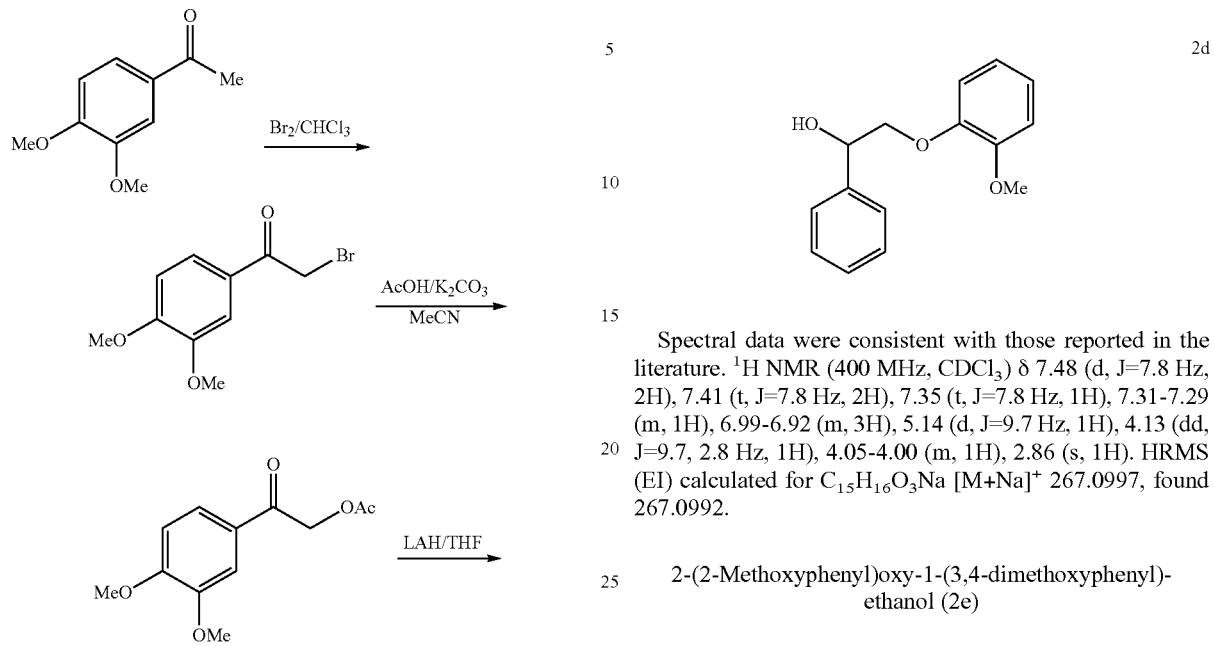

Scheme 7. Systhesis of 3,4-(Dimethoxyphenyl)ethyleneglycol (2b).

$^1$H — NMR: 6.91-6.82 (m, 3H), 4.76-4.73 (m, 1H), 3.87 (s, 3H), 3.86 (s, 3H), 3.73-3.62 (m, 2H), 2.56 (b s, 2H), HRMS (EI) calculated for $C_{10}H_{14}O_4$ [M + Na]$^+$ 221.0790, found 221.0785.

General Procedure for Preparing 2-aryloxy-1-phenethanols (2d, 2e, and 2f):

These substrates were synthesized in two steps from the corresponding phenol and 2-bromoacetophenone according to literature procedures. ((a) Kandanarachchi, P. H.; Autrey, T.; Franz, J. A. J. Org. Chem. 2002, 23, 7937. (b) Nichols, J. M.; Bishop, L. M.; Bergman, R. G., Ellman, J. A. J. Am. Chem. Soc. 2010, 132, 12554.) 2-Bromoacetophenone (5 mmol, 0.990 g) was added to a stirred solution of $K_2CO_3$ (7.5 mmol, 1.036 g) and guaiacol (6.25 mmol, 0.776 g) in acetone (50 mL). The reaction mixture was stirred at reflux temperature for 5 h, after which it was filtered off and concentrated under vacuum. The residue was purified by column chromatography with hexane:ethyl acetate (3:1). The resulting compound (3.5 mmol, 0.847 g) was dissolved in THF:$H_2O$ (5:1) (25 mL) and sodium borohydride (7 mmol, 0.26 g) was added drop-wise to maintain a gentle evolution of gas. Then, the mixture was stirred for 6 h at room temperature. The reaction mixture was quenched with saturated aqueous $NH_4Cl$ (50 mL) and diluted with 30 mL water. The aqueous portion was extracted with ethyl acetate (3×30 mL). The organic parts were combined, dried over $MgSO_4$, filtered and concentrated under vacuum. The residue purified by column chromatography with hexane:ethyl acetate (2:1).

2-(2-Methoxyphenyl)oxy-1-phenethanol (2d)

Spectral data were consistent with those reported in the literature. $^1$H NMR (400 MHz, CDCl$_3$) δ 7.48 (d, J=7.8 Hz, 2H), 7.41 (t, J=7.8 Hz, 2H), 7.35 (t, J=7.8 Hz, 1H), 7.31-7.29 (m, 1H), 6.99-6.92 (m, 3H), 5.14 (d, J=9.7 Hz, 1H), 4.13 (dd, J=9.7, 2.8 Hz, 1H), 4.05-4.00 (m, 1H), 2.86 (s, 1H). HRMS (EI) calculated for $C_{15}H_{16}O_3Na$ [M+Na]$^+$ 267.0997, found 267.0992.

2-(2-Methoxyphenyl)oxy-1-(3,4-dimethoxyphenyl)-ethanol (2e)

Spectral data were consistent with those reported in the literature. $^1$H NMR (400 MHz, CDCl$_3$) δ 7.03-6.99 (m, 2H), 6.98 6.90 (m, 4H), 6.86 (d, J=8.2 Hz, 1H), 5.06 (d, J=9.3 Hz, 1H), 4.16 (dd, J=9.3, 2.1 Hz, 1 H), 3.97 (m, 1H), 3.91 (s, 3H), 3.89 (s, 6H), 3.55 (b s, 1H). HRMS (EI) calculated for $C_{17}H_{20}O_5Na$ [M+Na]$^+$ 327.1209, found 327.1203.

2-(2,6-Dimethoxyphenyl)oxy-1-(3,4-dimethoxyphenyl)-ethanol (20

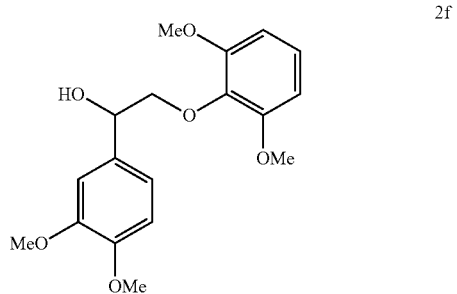

The reaction gave 84% overall yield in two steps. Colorless solid, mp. 127-128° C. $^1$H NMR (400 MHz, CDCl$_3$) δ 7.03 (t, J=8.4 Hz, 1H), 7.00-6.94 (m, 1H), 6.94-6.87 (m, 1H), 6.82 (d, J=8.2 Hz, 1H), 6.61 (d, J=8.4 Hz, 2H), 4.91 (dd, J=10.5, 2.5 Hz, 1H), 4.53 (b s, 1H), 4.39 (dd, J=11.0, 2.5 Hz, 1H), 3.87 (s, 9H), 3.85 (s, 3H), 3.70 (t, J=10.5 Hz, 1H). $^{13}$C NMR (100 MHz, CDCl$_3$) δ 153.39, 149.12, 148.66, 136.93, 132.16, 124.24, 118.81, 111.09, 109.54, 105.28, 80.29, 72.36, 56.25, 56.06, 56.02. HRMS (EI) calculated for C$_{17}$H$_{20}$O$_5$Na [M+Na]$^+$ 357.1314, found 357.1309.

Erythro-1-(3,4-dimethoxyphenyl)-2-(2-methoxyphenoxy)-1,3-propanediol (2g)

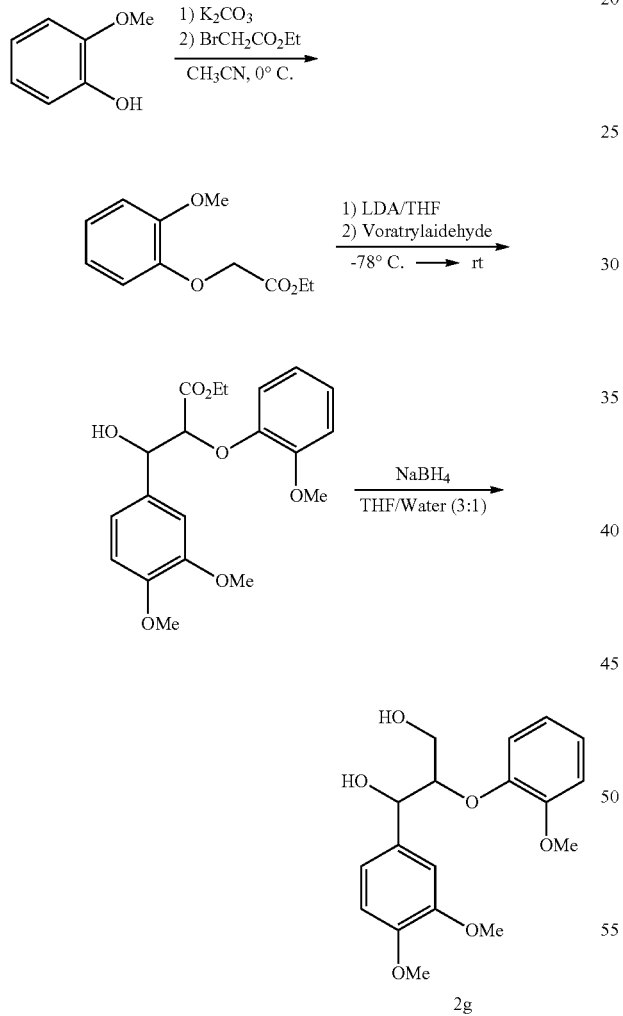

This compound was prepared according to a literature procedure. (Buendia, J.; Mottweiler, J.; Bolm, C. Chem. Eur. J. 2011, 17, 13877.) Spectral data were consistent with those reported in the literature. $^1$H NMR (400 MHz, CDCl$_3$) δ 7.07 (ddd, J=8.2 Hz, 7.2, 1.6, 1.6 Hz, 1H), 7.02-6.84 (M, 5H), 6.82 (D, J=8.2 Hz, 1H), 4.98 (b t, J=4.8 Hz, 1H), 4.16 (ddd, J=6.0, 4.8, 3.5 Hz, 1H), 3.95-3.90 (m, 1H), 3.87 (s, 3H), 3.86 (s, 6H), 3.66 (ddd, J=12.0, 7.2, 3.5 Hz, 1H), 2.87 ppm (b s, 1H). HRMS (EI) calculated for C$_{18}$H$_{22}$O$_6$Na [M+Na]$^+$ 357.1314, found 357.1311.

Erythro-1-(4-hydroxy-3-methoxyphenyl)-2-(2-methoxyphenoxy)-1,3-propanediol (2h)

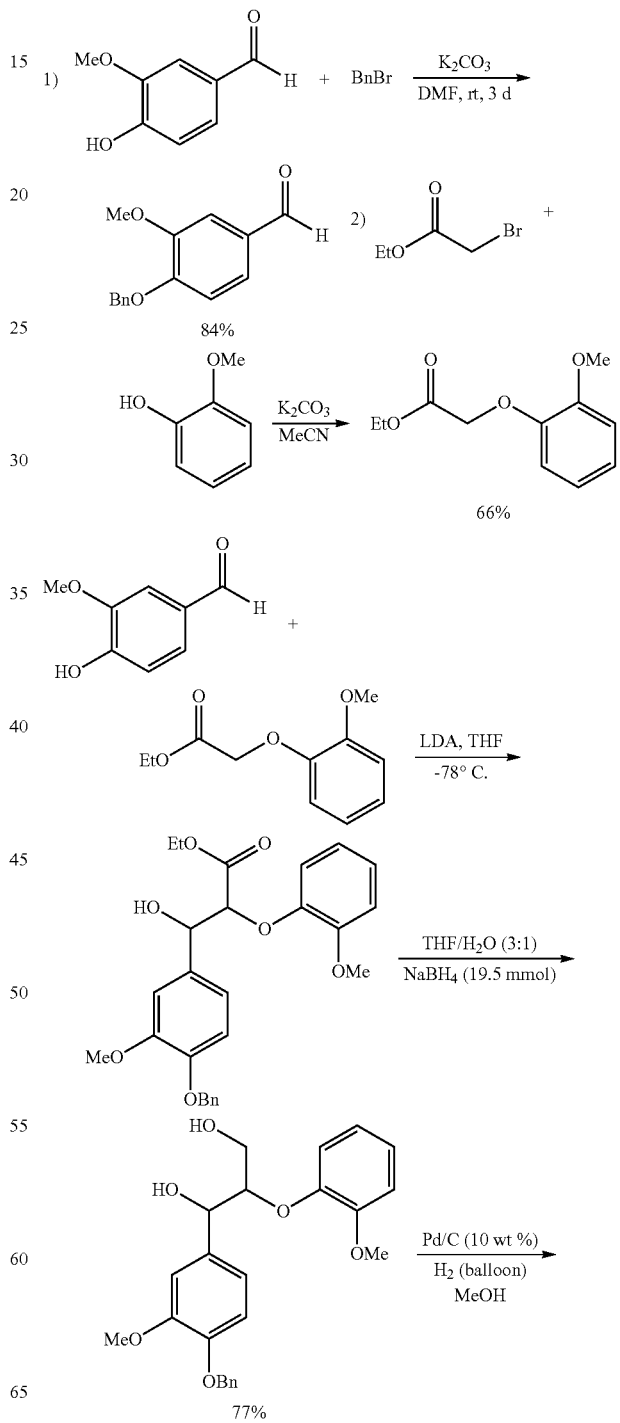

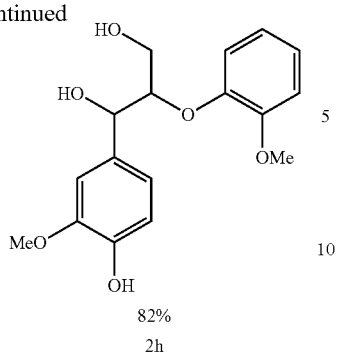

82%

2h

This compound was prepared according to the same literature procedure as for compound 2g. Spectral data were consistent with those reported in the literature. $^1$H NMR (400 MHz, CDCl$_3$) δ 7.16 (dd, J=8.2, 1.6 Hz, 1H), 7.04-6.86 (m, 5H), 6.86 (d, J=8.2 Hz, 1H), 5.71 (b s 1H), 4.96 (d, J=7.9 Hz, 1H), 4.06-3.97 (m, 1H), 3.90 (s, 3H), 3.87 (s, 3H), 3.73-3.58 (m, 2H), 3.48 (ddd, J=12.0, 7.8 and 3.6 Hz, 1H), 2.78-2.73 (m, 1H). HRMS (ESI) calculated for C$_{17}$H$_{20}$O$_6$Na [M+Na]$^+$ 343.1158, found 343.1154.

2-(2-Methoxyphenoxy)-1-(3,4,5-trimethoxyphenyl)-1,3-propanediol (2j)

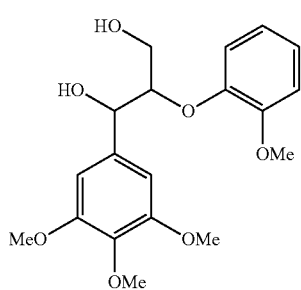

2j

This compound was prepared in the same fashion as 2g. This method resulted in the formation of a colorless sticky semi-solid in 66% overall yield, which was a mixture of the erythro:threo isomers (1.85:1). $^1$H NMR (300 MHz, CDCl$_3$) δ 7.10 7.00 (m, 4H, minor diastereomer), 6.94-6.87 (m, 4H, major diastereomer), 6.66 (s, 2H, minor diastereomer), 6.60 (s, 2H, major diastereomer), 4.96-4.92 (m, 2H, both diastereomers), 4.14 (ddd, J=6.1, 4.6, 3.2 Hz, 1 H, major diastereomer), 4.04 (ddd, J=6.1, 4.6, 3.2 Hz, 1 H, minor diastereomer), 3.87, 3.84, 3.83, 3.81 and 3.80 (all singlets for methoxy groups, 12H for any diastereomer), 370-3.61 (m, 1H, major diastereomer), 3.57-3.46 (m, 1H, minor diastereomer), 2.96 (b s, 2H, both diastereomer). $^{13}$C NMR (75 MHz, CDCl$_3$) major diastereomer: δ 153.39, 151.61, 147.02, 137.47, 135.89, 124.27, 121.74, 120.83, 112.33, 103.31, 89.15, 87.15, 73.14, 61.00, 56.29, 56.02; minor diastereomer: δ 153.43, 151.35, 147.68, 137.86, 135.52, 124.35, 121.82, 120.97, 112.33, 104.17, 89.15, 87.13, 74.26, 61.23, 60.97, 56.04. HRMS (EI) calculated for C$_{19}$H$_{24}$O$_7$NH$_4$ [M+NH4]$^+$ 382.1866, found 382.1861.

2-(2-Methoxyphenoxy)-1-(4-hydroxy-3,5-dimethoxyphenyl)-1,3-propanediol (2i)

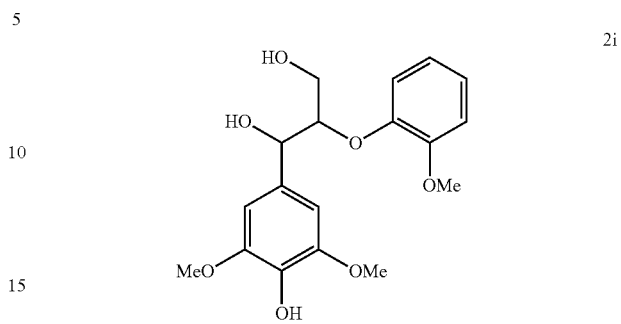

2i

This compound was prepared in same fashion as 2h and a literature procedure. (Pardini, V. L., Smith, C. Z., Utley, J. H. P., Vargas, R. R., Viertler, H. J. Org. Chem. 1991, 56, 7305.) $^1$H NMR (300 MHz, CDCl$_3$) δ 7.14 6.90 (m, 4H), 6.68 (s, 2H, minor diastereomer), 6.62 (s, 2H, major diastereomer), 5.55 (s, 1H, minor diastereomer, —OH), 5.52 (s, 1H, major diastereomer, —OH), 4.95 (m, 1H), 4.14 (m, 1H, major diastereomer), 4.00 (m, 1H, minor diastereomer), 3.91 (s, 3H, minor diastereomer), 3.89 (s, 3H, major diastereomer), 3.88 (s, 6H, minor diastereomer), 3.86 (s, 6H, major diastereomer), 3.70-3.62 (m, 1H, major diastereomer), 3.55-3.53 (m, 1H, minor diastereomer), 2.74 (b s, 1H). $^{13}$C NMR (75 MHz, CDCl$_3$) major diastereomer: δ 151.85, 147.32, 134.37, 131.19, 124.50, 121.89, 121.41, 112.41, 103.91, 102.9, 87.66, 73.14, 61.01, 56.58, 56.12; minor diastereomer: β 151.6, 147.10, 134.71, 130.86, 124.56, 121.95, 121.31, 112.41, 103.90, 102.91, 89.74, 74.47, 61.16, 56.58, 56.14. HRMS (EI) calculated for C$_{18}$H$_{22}$O$_7$NH$_4$ [M+NH4]$^+$368.1709, found 368.1704.

Figure 5:
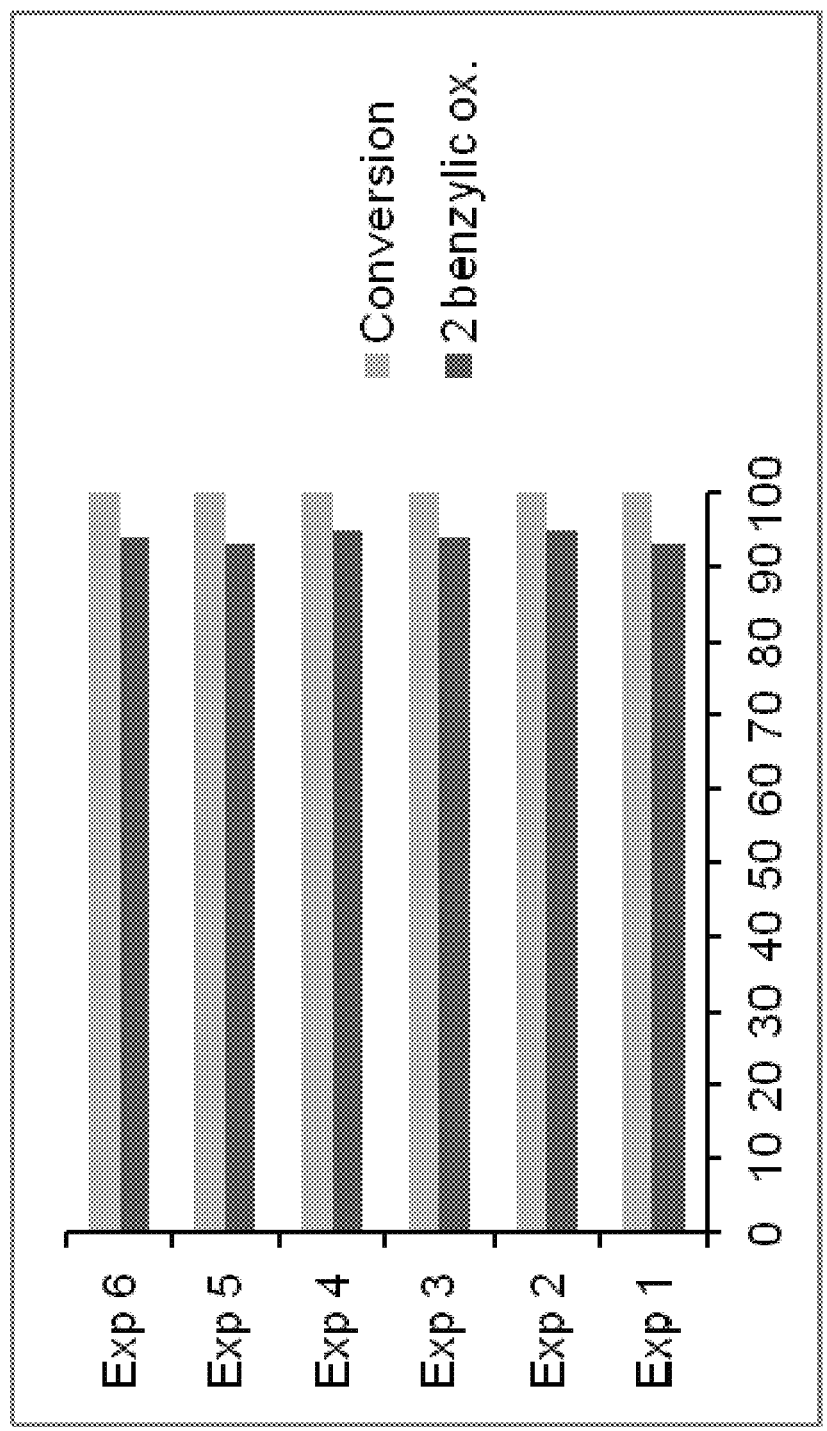
FIG. 5 is a histogram depicting yield and conversion of aerobic oxidation of compound 1 using HNO3/HCL/AA-TEMPO. Six (6) duplicate runs are shown, illustrating that the results are reproducible.

General Procedure for Oxidation of Lignin Model Compounds:

To a 25 mL high pressure tube with a stir bar was added lignin model compound (1 mmol) and 5 mol % of NHAc-TEMPO (0.05 mmol, 10.6 mg). The tube was sealed, evacuated and filled to 1.1 atm with oxygen gas. Nitric acid (67%; 9.4 μL) (0.1 mmol, 6.3 mg) in 1 mL acetonitrile and 9.9 μL of hydrochloric acid (37%) (0.1 mmol, 3.65 mg) in 1 mL of acetonitrile was injected through the septum individually. Additional 3 mL of acetonitrile and 260 μL of water were injected. The reaction mixture was stirred for 24 h at 45° C. The solvent was evaporated and the residue was subjected to column chromatography to ascertain the amount of the corresponding carbonyl compound. The reaction of 1 with optimized catalyst system was repeated several times. The results are shown in FIG. 5. As is clearly depicted in the figure, the conversion and yield results for this catalytic system (HNO$_3$/HCl/NHAc-TEMPO) are highly consistent. The six identical runs yielded statistically identical conversions and yields.

3,4-Dimethoxy-benzaldehyde (3a)

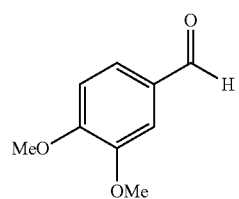

3a

Spectral data were consistent with those reported in the literature. (Jeena, V.; Robinson, R. S. Chem. Commun. 2012, 48, 299.) $^1$H NMR (400 MHz, CDCl$_3$) δ 9.86 (s, 1H), 7.47 (dd, J=8.2, 2.0 Hz, 1H), 7.41 (d, J=1.8 Hz, 1H), 6.97 (d, J=8.2 Hz, 1H), 3.97 (s, 3H), 3.95 (s, 3H). HRMS (EI) calculated for C$_9$H$_{10}$O$_3$ [M]$^+$166.0630, found 166.0626.

1-(3,4-Dimethoxyphenyl)-2-hydroxyacetone (3b)

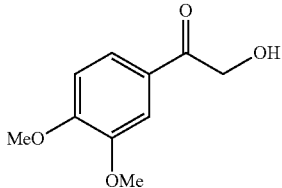

Spectral data were consistent with those reported in the literature. (same as ref for 2b) $^1$H NMR (400 MHz, CDCl$_3$) δ 7.50 (s, 1H), 7.49 (d, J=8.1 Hz, 1H), 6.91 (d, J=8.1 Hz, 1H), 4.84 (s, OH 2H), 3.95 (s, 3H), 3.94 (s, 3H), 3.55 (b s, 1H). HRMS (EI) calculated for C$_{10}$H$_{12}$O$_4$Na [M+Na]$^+$219.0633, found 219.0629.

2-Methoxy-1,2-diphenyl-ethanone (3c)

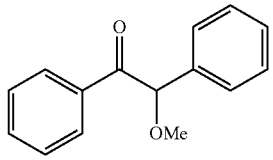

Spectral data were consistent with those reported in the literature. (Cutulic, S. P. Y.; Findlay, N. J.; Zhou, S Z.; Chrystal, E. J. T.; Murphy, J. A. J. Org. Chem. 2009, 74, 8713.) $^1$H NMR (400 MHz, CDCl$_3$) δ 8.00 7.98 (m, 2H), 7.52 7.45 (m, 3H), 7.41 2.27 (m, 3H), 5.52 (s, 1H), 3.46 (s, 3H). HRMS (EI) calculated for C$_{15}$H$_{15}$O$_2$ [M+H]$^+$ 227.1072, found 227.1075.

2-(2-Methoxyphenoxy)-1-phenyl-ethanone (3d)

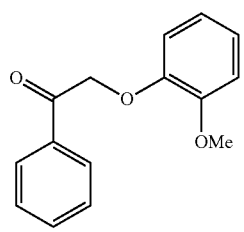

Spectral data were consistent with those reported in the literature. (same as ref 'b' in general procedure for preparation of 2d-f) $^1$H NMR (400 MHz, CDCl$_3$) δ 8.00 (d, J=8.0 Hz, 2H), 7.61 (d, J=7.6 Hz, 1H), 7.49 (t, J=7.6 Hz, 2H), 6.99 6.85 (m, 4H), 5.35 (s, 2H), 3.88 (s, 3H). HRMS (EI) calculated for C$_{15}$H$_{15}$O$_3$ [M+H]$^+$243.1021, found 243.1016.

2-(2-Methoxyphenoxy)-1-(3,4-dimethoxyphenyl)-ethanone (3e)

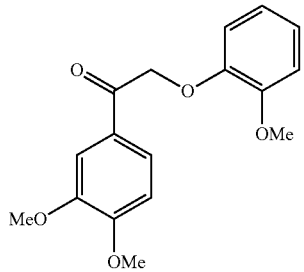

Spectral data were consistent with those reported in the literature. (same as ref 'b' in general procedure for preparation of 2d-f) $^1$H NMR (400 MHz, CDCl$_3$) δ 7.67 (dd, J=7.8, 1.8 Hz, 1H), 7.60 (d, J=7.8 Hz, 1H), 6.96 6.83 (m, 5H), 5.29 (s, 2H), 3.95 (s, 3H), 3.93 (s, 3H), 3.88 (s, 3H). HRMS (EI) calculated for C$_{17}$H$_{19}$O$_5$ [M+H]$^+$ 303.1232, found 303.1227.

2-(2,6-Dimethoxyphenoxy)-1-(3,4-dimethoxyphenyl)-ethanone (3f)

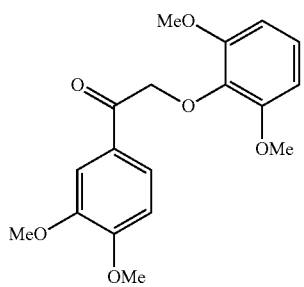

Spectral data were consistent with those reported in the literature. (Hurrell, L.; Johnston, L. J.; Mathivanan, N.; Vong, D. Can. J. Chem. 1993, 71, 1340.) $^1$H NMR (300 MHz, CDCl$_3$) δ 7.70 (dd, J=8.4, 2.0 Hz, 1H), 7.62 (d, J=2.0 Hz, 1H), 6.98 (t, J=8.4 Hz, 1H), 6.87 (d, J=8.4 Hz, 1H), 6.56 (d, J=8.4 Hz, 2H), 5.12 (s, 2H), 3.91 (s, 6H), 3.78 (s, 6H). HRMS (EI) calculated for C$_{18}$H$_{21}$O$_6$ [M+H]$^+$ 333.1338, found 333.1333.

1-(3,4-Dimethoxyphenyl)-3-hydroxy-2-(2-methoxyphenoxy)-1-propanone (3g)

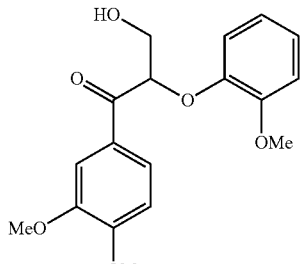

Spectral data were consistent with those reported in the literature. (See reference cited for compound 2b.) $^1$H NMR (400 MHz, CDCl$_3$) δ 7.74 (dd, J=8.2, 2.0 Hz, 1H), 7.62 (d, J=2.0 Hz, 1H), 7.01 6.83 (m, 5H), 5.39 (t, J=5.6 Hz, 1H), 4.07 (t, J=5.6, 2H), 3.95 (s, 3H), 3.92 (s, 3H), 3.86 (s, 3H), 2.97 (b s, 1H). HRMS (EI) calculated for C$_{18}$H$_{20}$O$_6$Na [M+Na]$^+$ 355.1158, found 355.1153.

1-(4-Hydroxy-3-methoxyphenyl)-3-hydroxy-2-(2-methoxyphenoxy)-1-propanone (3h)

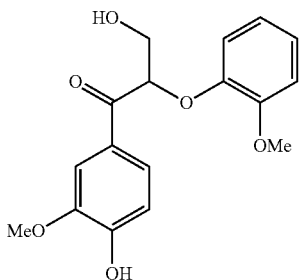

3h

Spectral data were consistent with those reported in the literature. (Badamali, S. K.; Luque, R.; Clark, J. H.; Breeden, S. W. Catalysis Communications 2011, 12, 993.) $^1$H NMR (400 MHz, CDCl$_3$) δ 7.69 (dd, J=8.2, 1.9 Hz, 1H), 7.61 (d, J=1.9 Hz, 1H), 7.01-6.79 (m, 5H), 6.38 (b s, 1H), 5.41 (t, J=5.2 Hz, 1H), 4.08 (d, J=4.1 Hz, 2H), 3.90 (s, 3H), 3.84 (3H), 3.18 (b s, 1H). $^{13}$C NMR (100 MHz, CDCl$_3$) δ 195.1, 151.4, 150.6, 147.1, 147.1, 127.9, 124.4, 123.7, 121.4, 118.4, 114.3, 112.5, 111.0, 84.5, 63.9, 56.3, 56.0. HRMS (ESI) calculated for C$_{17}$H$_{18}$O$_6$Na [M+Na]$^+$ 341.1001, found 341.1005.

1-(3,4,5-Trimethoxyphenyl)-3-hydroxy-2-(2-methoxyphenoxy)-1-propanone (3j)

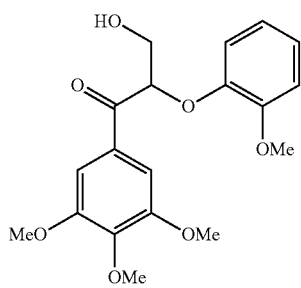

3j $^1$H NMR (400 MHz, CDCl$_3$) δ 7.36 (s, 2H), 7.01 (dd, J=7.6, 2.0 Hz, 1H), 6.93-6.89 (m, 2H), 6.84 (dd, J=7.8, 2.0 Hz, 1H), 5.36 (t, J=5.3 Hz, 1H), 4.09 (d, J=5.3 Hz, 2H), 3.92 (s, 3H), 3.88 (s, 6H), 3.85 (s, 3H), 3.17 (b s, 1H). $^{13}$C NMR (100 MHz, CDCl$_3$) δ 195.8, 153.3, 150.6, 147.0, 143.4, 130.2, 123.9, 121.4, 118.3, 112.5, 106.7, 84.7, 63.7, 61.2, 56.5, 56.0. HRMS (ESI) calculated for C$_{19}$H$_{22}$O$_7$Na [M+Na]$^+$ 385.1263, found 385.1267.

1-(4-Hydroxy-3,5-dimethoxyphenyl)-3-hydroxy-2-(2-methoxyphenoxy)-1-propanone (3i)

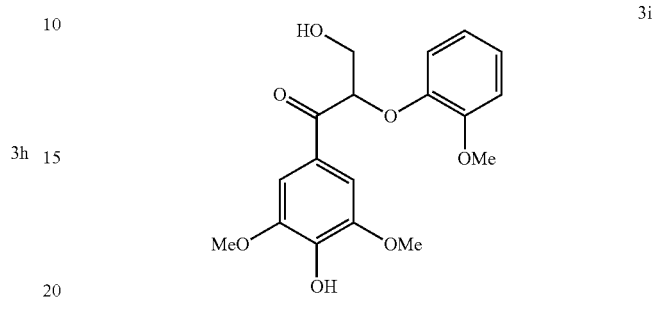

3i

Spectral data were consistent with those reported in the literature. (Vanholme, R.; Demedts, B.; Morreel, K.; Ralph, J.; Boerjan, W. *Plant Physiology,* 2010, 153, 895.) $^1$H NMR (400 MHz, CDCl$_3$) δ 7.42 (s, 2H), 7.02-6.86 (m, 4H), 6.02 (s, 1H), 5.39 (t, J=4.6 Hz, 1H), 4.11 (d, J=4.6 Hz, 2H), 3.85 (s, 6H), 3.83 (s, 3H), 3.08 (b s, 1H). $^{13}$C NMR (100 MHz, CDCl$_3$) δ 195.4, 150.8, 147.2, 140.8, 126.7, 124.0, 121.6, 118.4, 112.6, 106.8, 105.3, 84.9, 63.9, 56.8, 56.1. HRMS (ESI) calculated for C$_{18}$H$_{20}$O$_7$Na [M+Na]$^+$371.1107, found 371.1103.

Oxidation of Authentic Aspen Lignin Sample by HNO$_3$/HCl/NHAc-TEMPO:

To a 10 mL high-pressure tube with a stir bar was added 20 mg of aspen tree lignin and 1 mg of NHAc-TEMPO. The tube was sealed, evacuated and filled to 3 atm with oxygen gas. Nitric acid (1.5 μL, 67%) in 1 mL acetonitrile and 1 μL of hydrochloric acid (37%) in 1 mL of acetonitrile were injected through the septum individually. In addition, 100 μL of water was injected. The reaction mixture was stirred for 24 h at 65° C. The mixture was cooled and slowly depressurized. The solvent was evaporated and the residue was washed with chloroform and hexane to remove all small organic compounds. A light brown solid, 13.5 mg in weight, was dissolved in DMSO (d$_6$)/pyridine (d$_5$) (4:1) for 2-D NMR studies. Comparing the NMR spectra before oxidation (FIG. 4A) and after oxidation (FIG. 4B) shows that secondary benzylic alcohols were oxidized to corresponding carbonyl groups selectively. In short, see FIG. 4A, which is the NMR spectrum before oxidation as compared to FIG. 4B, which is the NMR spectrum after oxidation. FIG. 4C is the color-coded assignment of peaks by substituent type for FIGS. 4A and 4B.

Reductive Cleavage of Oxidized Lignin Model Compound:

Here, model compound 1, was used as the model compound for feasibility studies. Model compound 1 was fabricated by the following scheme:

Scheme 10. Formation and reductive cleavage of model compound 1. (See the earlier Examples for the synthesis of the other model compounds.)

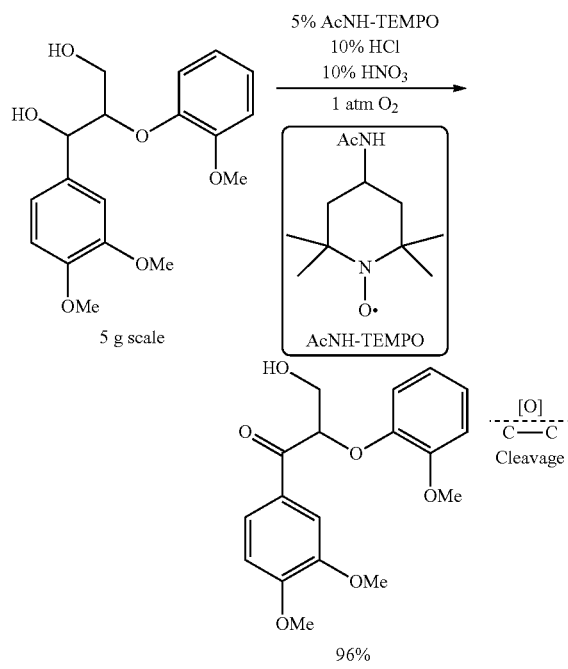

Compound 1 was then subjected to various reactions to selectively cleave the C—C and/or C—O bonds of the β-O-4 linkage between the two subunits of the dimer. The following reaction depicts reductive cleavage using formic acid in the presence of various metals. The reaction below recites zinc powder. The reaction was also run using iron, magnesium, or aluminum.

Scheme 11. Reductive cleavage of model compound 1.

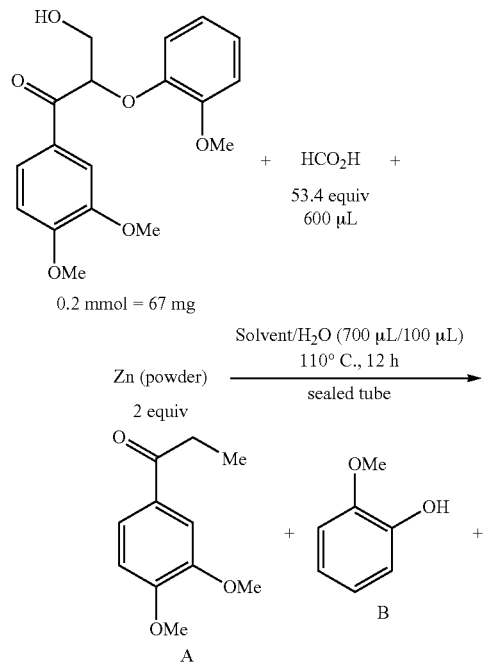

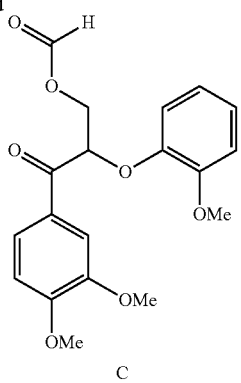

Figure 6:
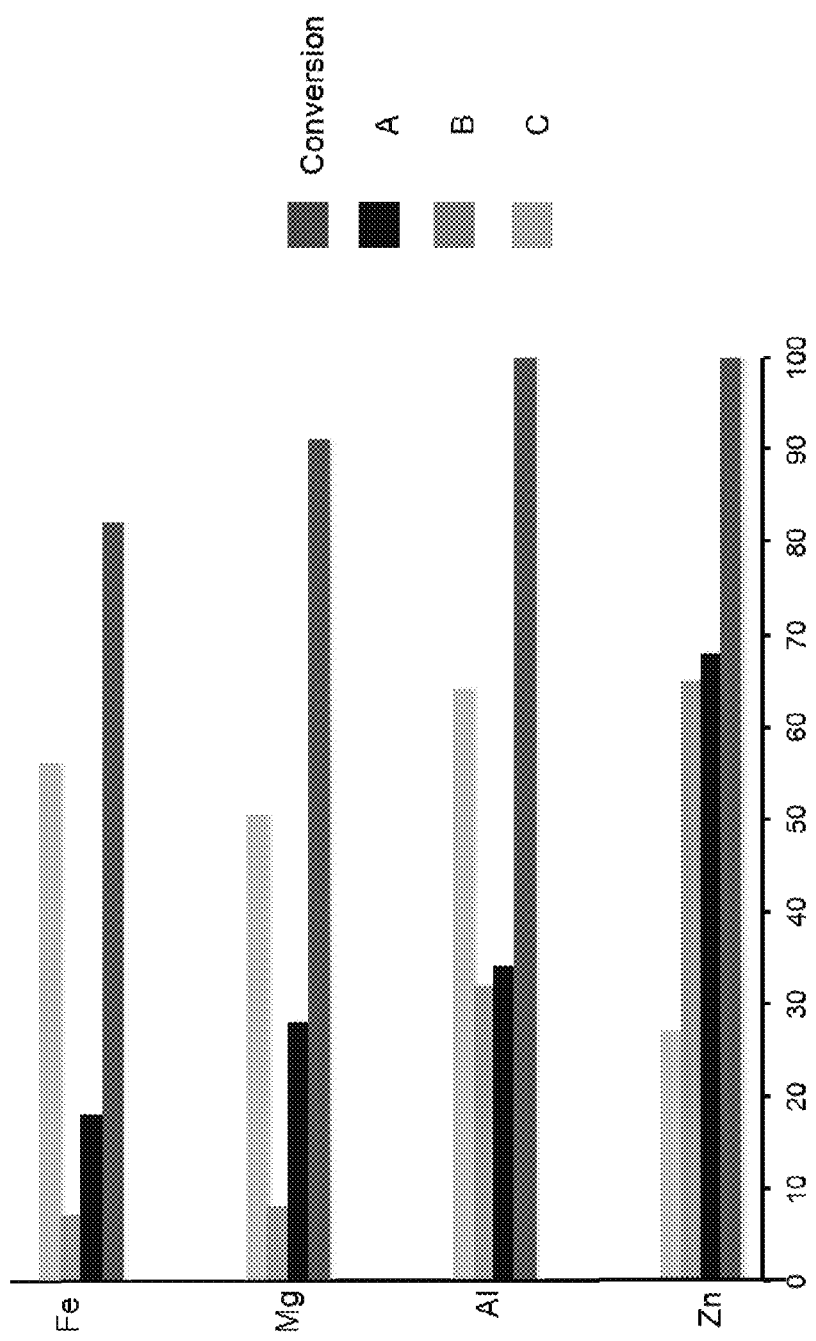
FIG. 6 is a histogram depicting reductive cleavage of oxidized lignin model compound 1 using formic acid in the presence of various metal catalysts (Fe, Mg, Al, and Zn).

See FIG. 6 for a graphic presentation of product yields. As can be seen from FIG. 6, overall conversion of the model compound to specific products was quite high. Conversion was over 80% for all conditions tested. Conversion was quantitative in the case of reactions using aluminum and zinc. See the two bottom entries in FIG. 6. Notably, conversion to the three compounds designated A, B, C in the Scheme 11 dominated the product mix. These data indicate that the specific cleavage of bonds within the β-O-4 linkage occurred.

Reductive Cleavage of Oxidized Lignin Model Compound:

In this Example, model compounds bearing a benzylic ketone group and a primary alcohol (Scheme 14) or a benzylic ketone group and aldehyde (Scheme 13) were subjected to cleavage using formic acid in water and in the presence of various metals, as well as in the absence of metals. The amount of metal catalyst and the acidity of the reaction medium were varied as shown in Scheme 12. Scheme 13 depicts the reaction and product yield under specific conditions that resulted in optimum yield.

Scheme 12. Reductive cleavage of model compound with primary alcohol group.

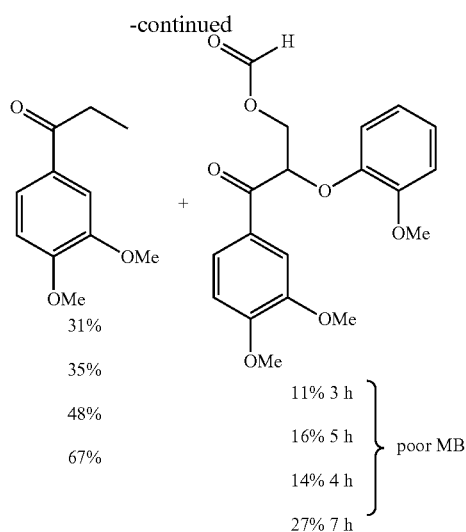

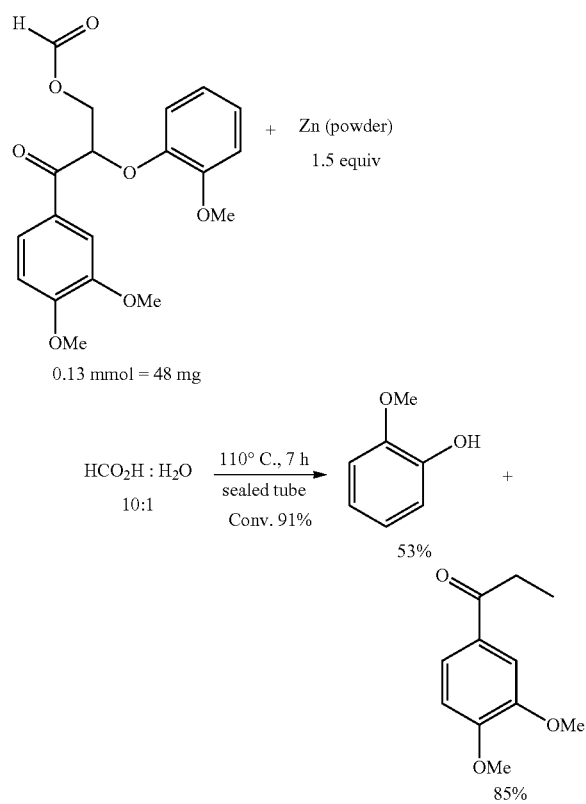

As shown in Schemes 12 and 13, the desired products were obtained in all instances, although yields were varied. However, by optimizing reaction conditions, yields could be dramatically improved. See, for example, the last entry of Scheme 12, in which the conversion was quantitative, with the first two simple aromatic compounds being yielded in 64.5% and 67% of theoretical yield, respectively. Scheme 13 presents a set of reaction conditions in which conversion was quite high at 91% with very good yield of simple aromatic compounds 53% and 85% of theoretical for the two listed products. These results are significant in that they demonstrate that the C—O and C—C bonds in the oxidized version of the β-O-4 linkage (that is, a β-O-4 linkage having a benzylic-position ketone) can be cleaved selectively to yield predictable, small aromatic compounds in good yield.

C—O Cleavage of Oxidized Sample in Different Solvents:

Reaction Scheme 14 depicts cleavage of a model compound in formic acid in the presence of powdered zinc.

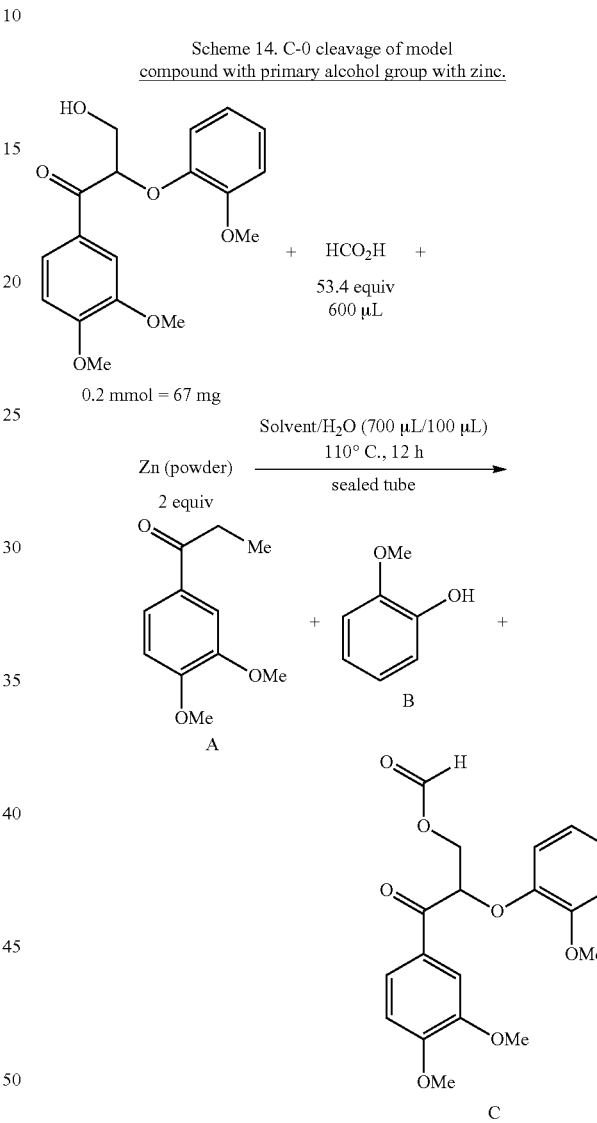

Figure 7:
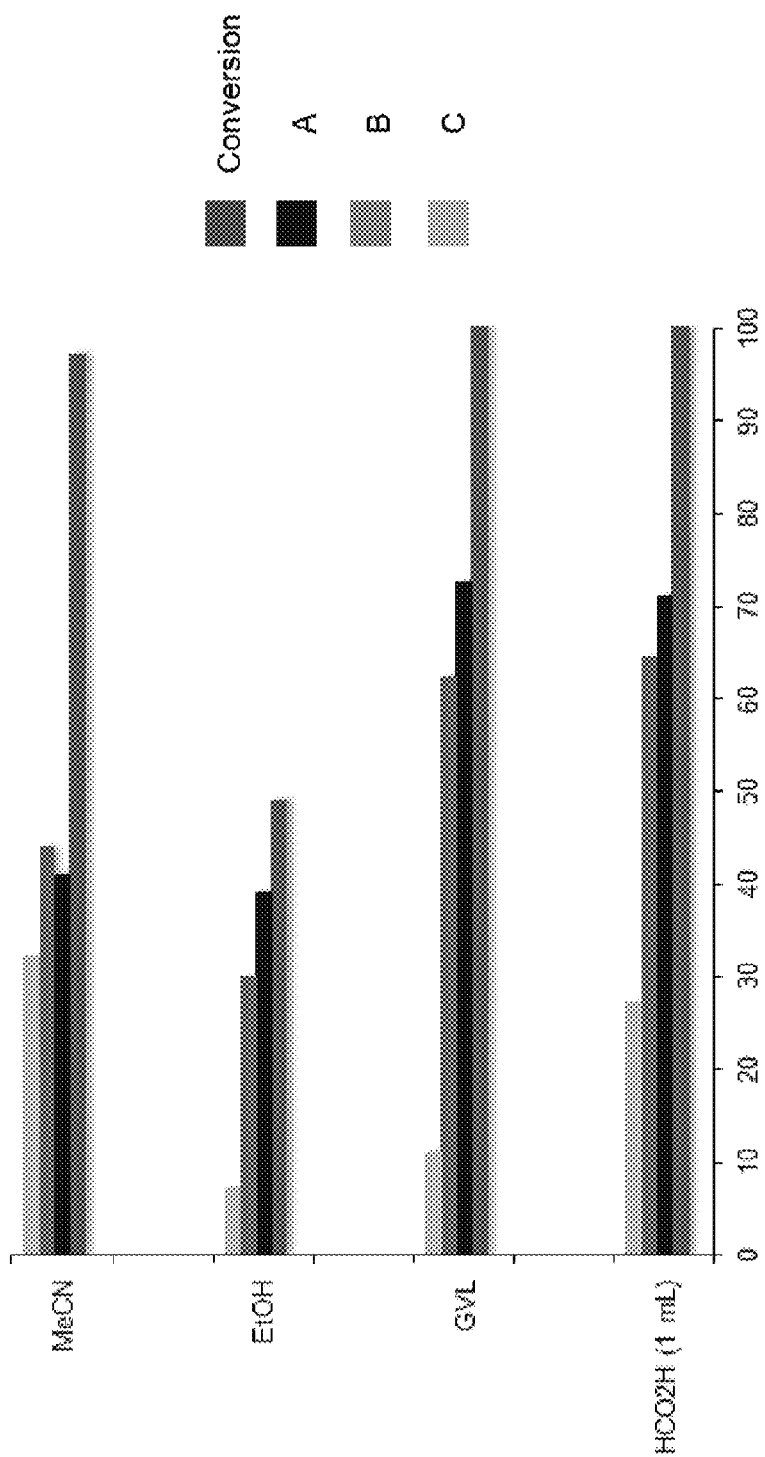
FIG. 7 is a histogram depicting C—O cleavage of an oxidized sample in different solvent systems (acetonitrile (MeCN), ethanol (EtOH), gamma-valerolactone (GVL) and formic acid).

This same reaction was also run under identical reaction conditions using acetonitrile, ethanol, or GVL as the solvent. The results are depicted in FIG. 7. As shown in the figure, conversion was essentially quantitative using acetonitrile, GVL and formic acid as solvents. Conversion in ethanol was considerably less, at slightly over 50% of theoretical. Nevertheless, specificity to product A as shown in Scheme 14 was quite good (>70% of theoretical) when GVL or formic acid was used as the solvent. See the final two entries of FIG. 7.

C—O Cleavage of Oxidized Sample without Metal:

Further testing revealed that selective cleavage of bond in the β-O-4 linkage could be accomplished using an acid and without a metal catalyst. An exemplary reaction using model compound 1 (which includes a benzyl-position ketone) and aqueous formic acid is depicted in Scheme 15. Scheme 16 depicts a control reaction using the unoxidized analog of model compound 1. That is, the reactant in Scheme 1 had a benzyl-position secondary alcohol group, rather than a ketone as in model compound 1.

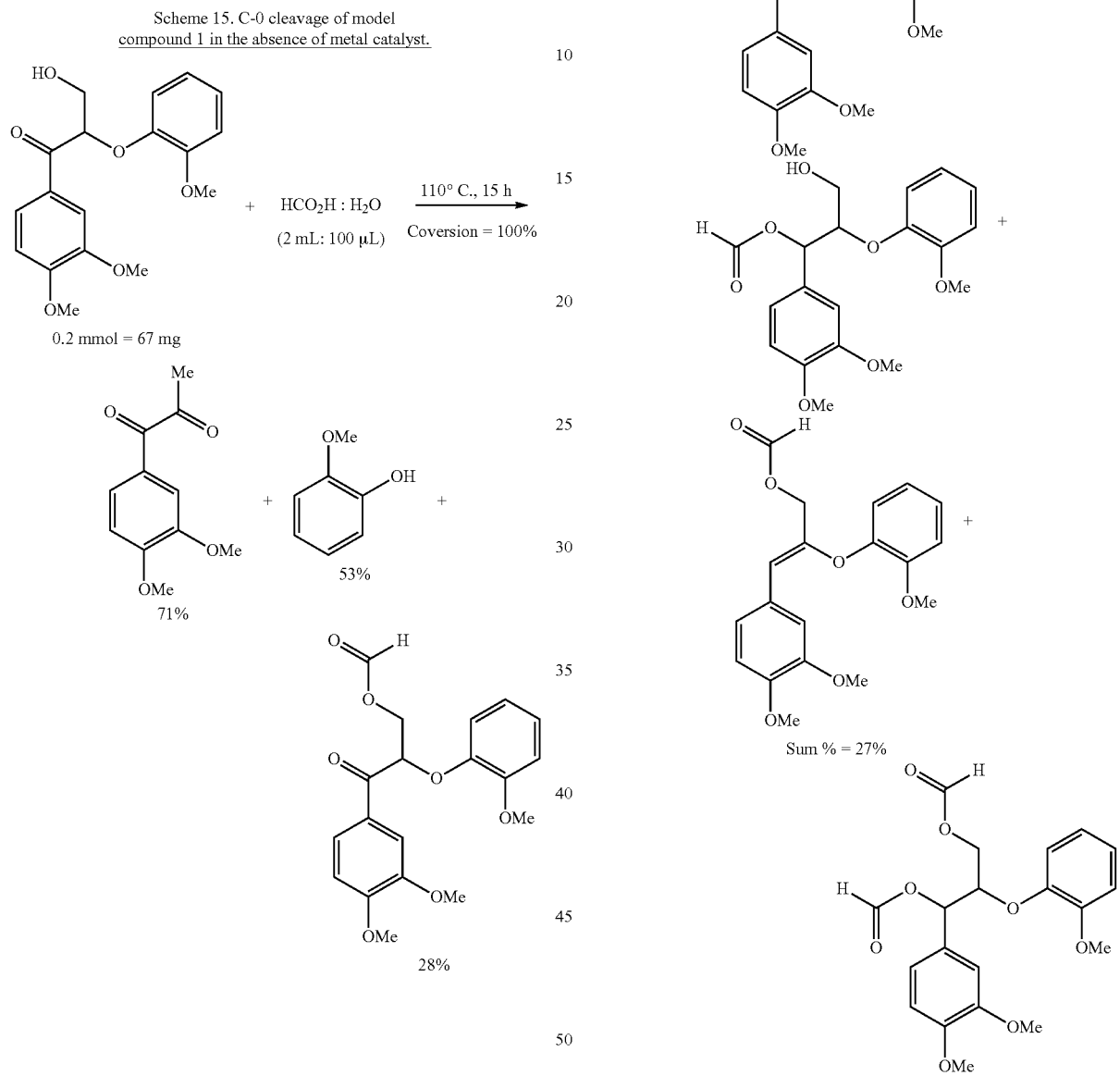

As shown in Scheme 15 versus Scheme 16, the presence of a benzylic ketone group has a profound impact on the selectivity of the reaction and the completeness of the reaction. Scheme 15 gave quantitative conversion to products and good yields of small, aromatic products (71% and 53% of theoretical yield). Scheme 16, in contrast, used a model compound without a benzyl-position ketone. In Scheme 16, conversion dropped to 83%, with a host of different dimeric products accounting for 27% of the product yield.

Proposed Mechanism:

While not being limited to any specific underlying mechanism, the presence of the benzylic ketone is thought to result in the mechanism depicted in Scheme 17.

Scheme 17. Proposed mechanism of C-O bond cleavage within β-O-4 linkage.

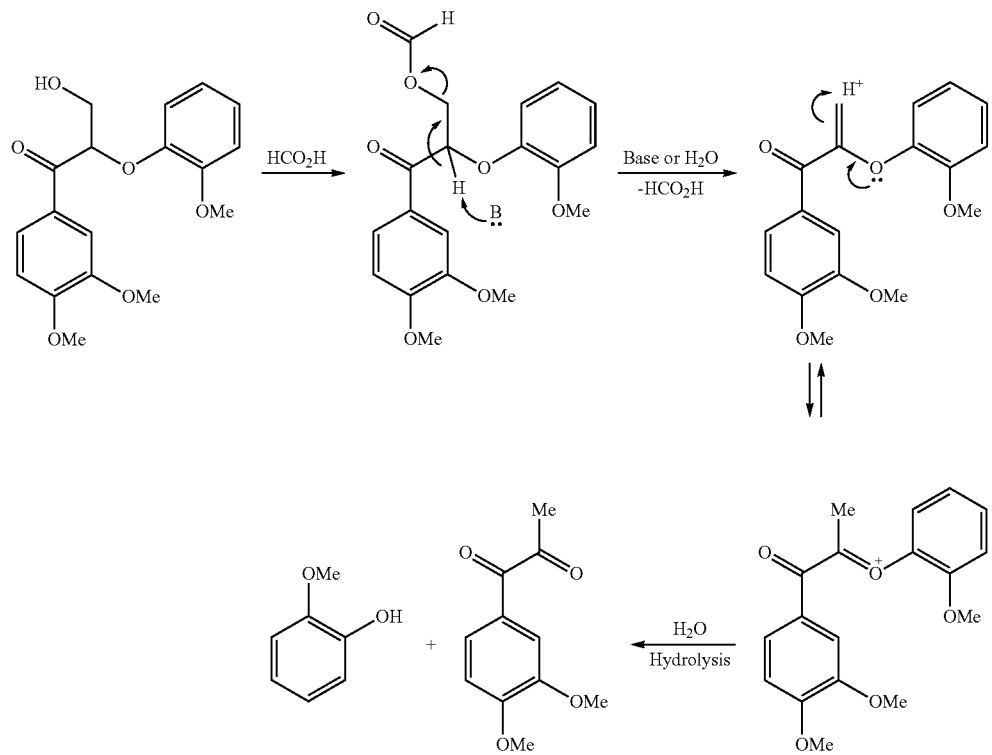

As shown in Scheme 17, formylation of the primary alcohol group in the β-O-4 linkage of model compound 1 is followed by an elimination reaction that liberates formic acid from the intermediate. This is followed by an electron rearrangement and the addition of water to the carbanion intermediate. This yields the intermediate in the bottom-right of Scheme 17. A subsequent electron rearrangement results in the cleavage of the C—O bond in the β-O-4 linkage.

C—O Cleavage of Different Oxidized Lignin Model Compounds:

Schemes 17 and 18 show that the approach described herein also function for other oxidized, lignin model compounds. Of particular note here is that all of the model compounds include a ketone in the benzyl position (i.e., the α-position) of the β-O-4 linkage.

Scheme 18. C-O Cleavage of various model compounds.

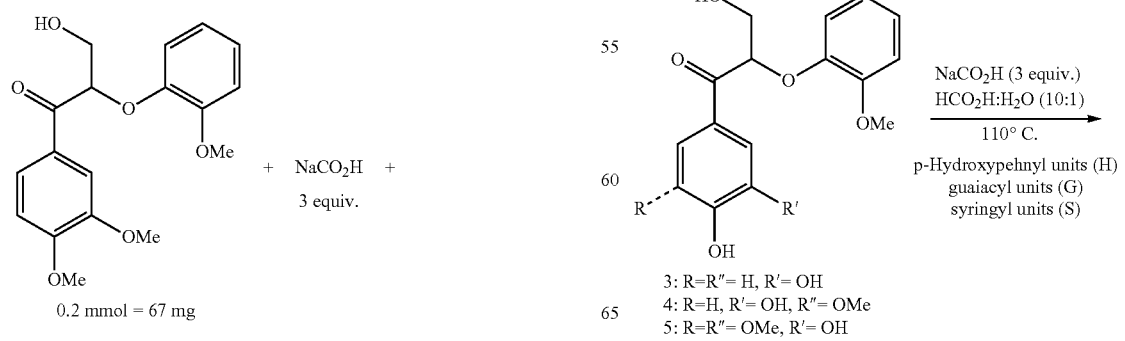

-continued

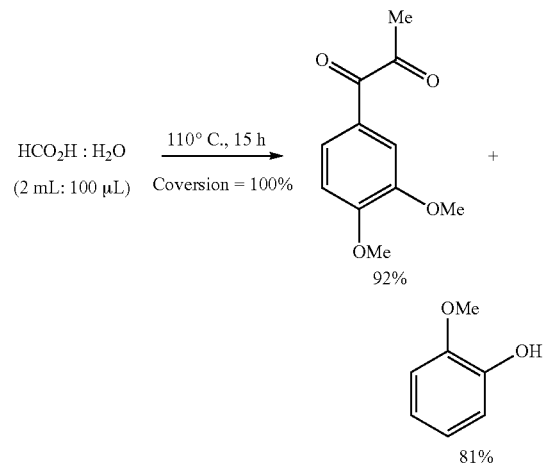

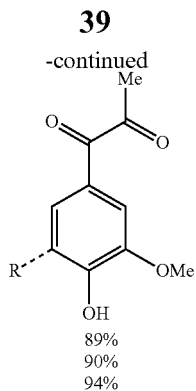

89%
90%
94%

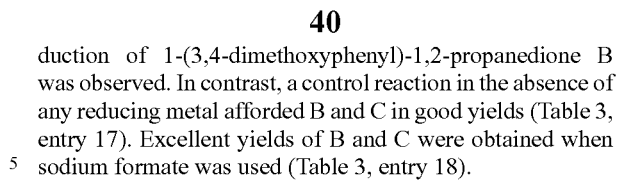

73%
84%
88%

As shown in Scheme 18, the specific yield of small, aromatic compounds was quite high.

Figure 8:
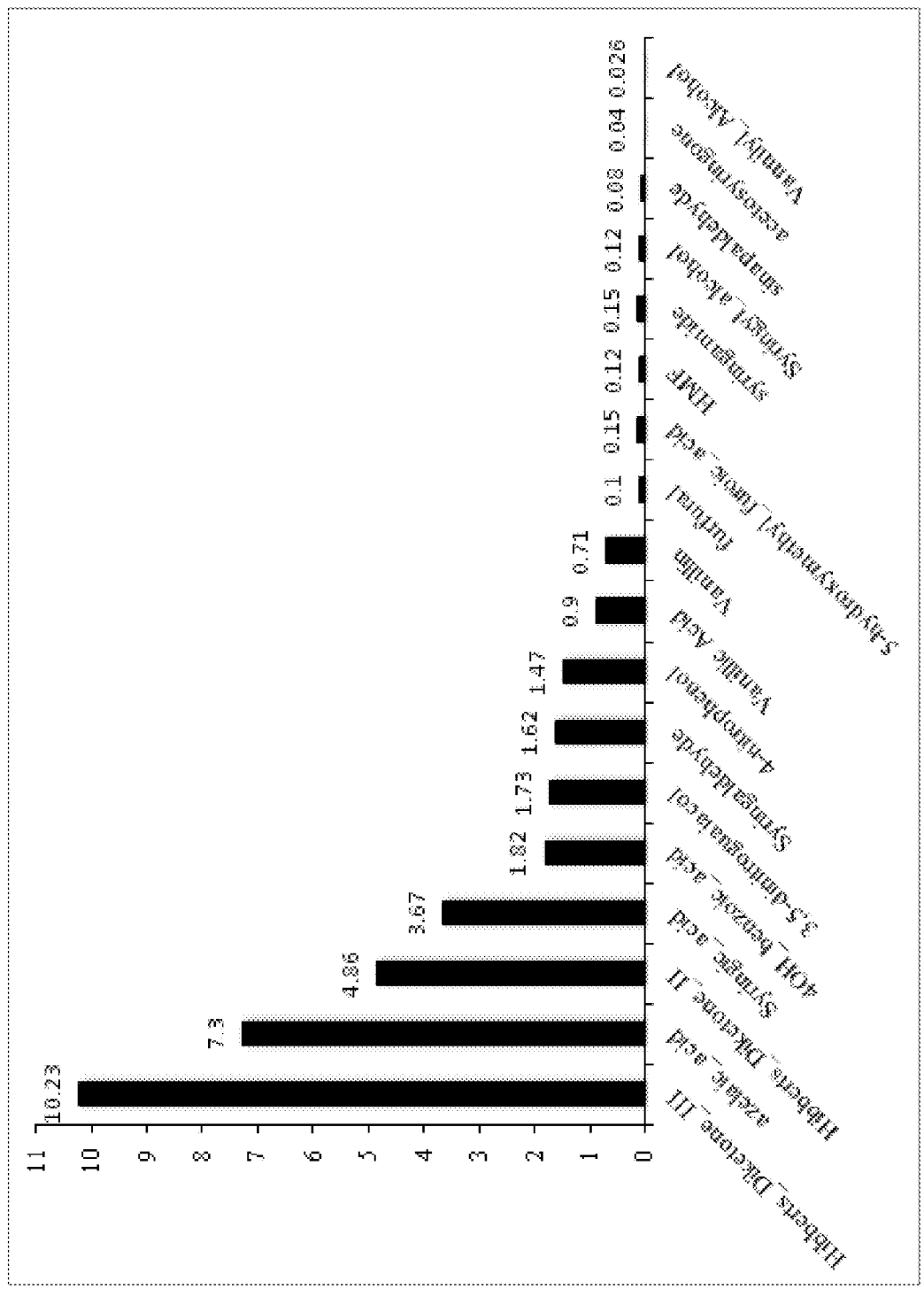
FIG. 8 is histogram depicting the product yield of small organic compounds via the selective C—O cleavage of oxidized lignin using the method disclosed herein.

C—O Cleavage of Oxidized Lignin to Simple Chemicals:

Here, an authentic lignin sample was oxidized to introduce a benzylic-position ketone in at least a portion of the β-O-4 linkages, and then subjected to depolymerization via C—O cleavage of the ether bond in the β-O-4 linkages. The resulting product mixture is shown in FIG. 8.

Discussion of Examples

Overall, the Examples used oxidized lignin model compounds to develop an efficient depolymerization technique. Initial tests were carried out with readily available reducing metals under various reaction conditions. See Table 3. Applying zinc powder more than one equivalent in a mixture of formic acid and water afforded 1-(3,4-dimethoxyphenyl)-1-propanone A and guaiacol C as a major products under mild reaction conditions. See Table 3, entries 2-3 and 7-8. Additionally, formylation of alcohol groups in the oxidized lignin model compounds resulted in D, which was identified in all reactions. However, no C—O cleavage of 2 with mineral acids or acetic acid in the presence of zinc powder was observed. See Table 3, entries 4-6. When acetic acid was used, acetylation of the alcohol functional group in 2 was the only reaction product. This reaction was performed in organic solvents such as ethanol and gamma-valerolactone (GVL). Ethanol worked as a solvent, but was not as effective for this transformation (Table 3, entry 7). GVL resulted in formation of A and C in 71% and 61.5% yields, respectively (Table 3, entry 8). The performance of other reducing metals, such as aluminum, magnesium, iron, and manganese were also investigated (Table 3, entries 11-14). Poor reactivity for the production of 1-(3,4-dimethoxyphenyl)-1,2-propanedione B was observed. In contrast, a control reaction in the absence of any reducing metal afforded B and C in good yields (Table 3, entry 17). Excellent yields of B and C were obtained when sodium formate was used (Table 3, entry 18).

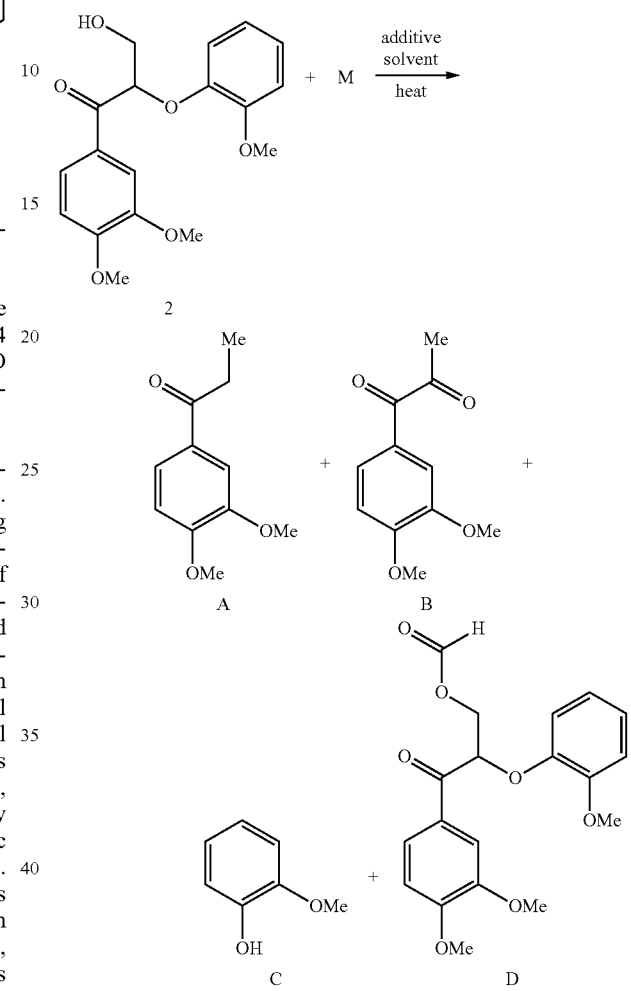

TABLE 3

C—O cleavage of 2 under different reaction conditions.[a]

| entry | M (equiv) | additive (equiv) | solvent | T (°C.) | t (h) | A (%) | B (%) | C (%) | D (%) | conversion (%) |
|---|---|---|---|---|---|---|---|---|---|---|
| 1 | Zn (1) | | HCO$_2$H:H$_2$O (1:1) | 100 | 3 | 31 | 2 | 28 | 11.1 | 59 |
| 2 | Zn (1.5) | | HCO$_2$H:H$_2$O (1:1) | 100 | 4 | 48 | 0 | 32 | 13.8 | 86 |
| 3 | Zn (2) | | HCO$_2$H:H$_2$O (1:1) | 100 | 5 | 35 | 0 | 31 | 16.6 | 89 |
| 4 | Zn (1.5) | | CH$_3$CO$_2$H:H$_2$O (1:1) | 100 | 5 | 0 | 0 | 0 | 0 | 41 |
| 5 | Zn (2) | H$_2$SO$_4$ (2) | ethanol | reflux | 6 | 0 | 0 | 0 | 0 | 0 |
| 6 | Zn (2) | HCl (2) | toluene | Reflux | 6 | 0 | 0 | 0 | 0 | 0 |
| 7 | Zn (2) | HCO$_2$H (53.4) | ethanol:H$_2$O (7:1) | Reflux | 12 | 38.6 | 0 | 30 | 7 | 49 |
| 8 | Zn (2) | HCO$_2$H (53.4) | GVL:H$_2$O (7:1) | 110 | 12 | 71 | 0 | 62.5 | 11 | 91 |
| 9 | Zn (2) | — | GVL:H$_2$O (7:1) | 110 | 10 | 0 | 0 | 0 | 0 | 0 |
| 10 | — | HCO$_2$H (53.4) | GVL:H$_2$O (7:1) | 110 | 12 | 0 | 8 | 4.5 | 55 | 72 |
| 11 | Al(2) | HCO$_2$H (53.4) | GVL:H$_2$O (7:1) | 110 | 12 | 0 | 34 | 32 | 29 | 65 |
| 12 | Mg (2) | HCO$_2$H (53.4) | GVL:H$_2$O (7:1) | 110 | 12 | 0 | 28 | 8 | 50.5 | 87 |
| 13 | Fe(2) | HCO$_2$H (53.4) | GVL:H$_2$O (7:1) | 110 | 12 | 0 | 18 | 7 | 56 | 82 |
| 14 | Mn (2) | HCO$_2$H (53.4) | GVL:H$_2$O (7:1) | 110 | 12 | 0 | 37 | 19 | 47 | 93 |
| 15 | Mn (2) | — | HCO$_2$H:H$_2$O (10:1) | 110 | 12 | 0 | 73 | 69 | 19 | 100 |

TABLE 3-continued

C—O cleavage of 2 under different reaction conditions.[a]

| entry | M (equiv) | additive (equiv) | solvent | T (° C.) | t (h) | A (%) | B (%) | C (%) | D (%) | conversion (%) |
|---|---|---|---|---|---|---|---|---|---|---|
| 16 | Zn (1) | — | HCO$_2$H:H$_2$O (10:1) | 110 | 12 | 49 | 31 | 62 | 12 | 100 |
| 17 | — | — | HCO$_2$H:H$_2$O (10:1) | 110 | 16 | 0 | 71 | 53 | 28 | 100 |
| 18 | — | NaCO$_2$H (3) | HCO$_2$H:H$_2$O (10:1) | 110 | 15 | 0 | 92 | 81 | 0 | 100 |

[a] all reactions have been done in 0.1 mmol scale in 1.1 mL of solvent.
[b] conversion and yields were determined by $^1$H NMR spectroscopy versus mesitylene as internal standard (relaxation time = 20 s).

Without being limited to any underlying mechanism (and referring to the header of Table 3), these results suggest that hydrolysis of the C—O bond resulted in diketone B and then in the presence of zinc powder it reduced to A. Additionally, no reducing metal is needed for this transformation. The full reaction conditions associated with entry 18 featured heating the oxidized lignin model compound 2 in a mixture of formic acid/water (ratio: 10/1) in the presence of three equivalents of sodium formate. This method is quite effective for C—O cleavage of oxidized guaiacyl (G)- and syringyl-type phenols units in lignin (3 and 4) to desired products in excellent yields. See Scheme 19:

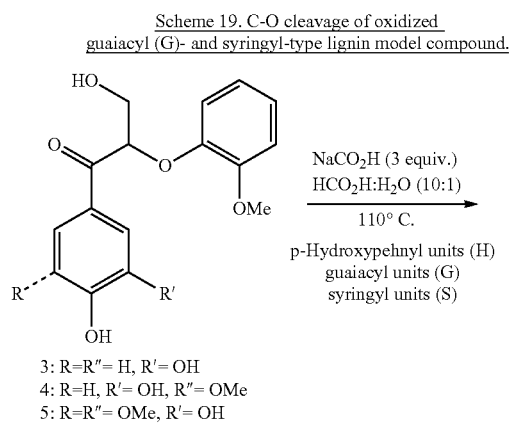

Scheme 19. C-O cleavage of oxidized guaiacyl (G)- and syringyl-type lignin model compound.

3: R=R″= H, R′= OH
4: R=H, R′= OH, R″= OMe
5: R=R″= OMe, R′= OH

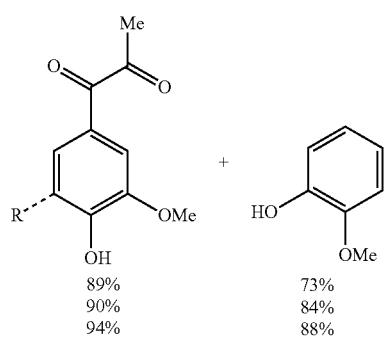

89%    73%
90%    84%
94%    88%

Most notably, however, is that the method works when the reactant is actual lignin, rather than a model compound. Treatment of an oxidized Aspen lignin sample in a mixture of formic acid and water in the presence of sodium formate afforded more than 25 wt % of low molecular weight chemicals (Chart 1) with the same selectivity.

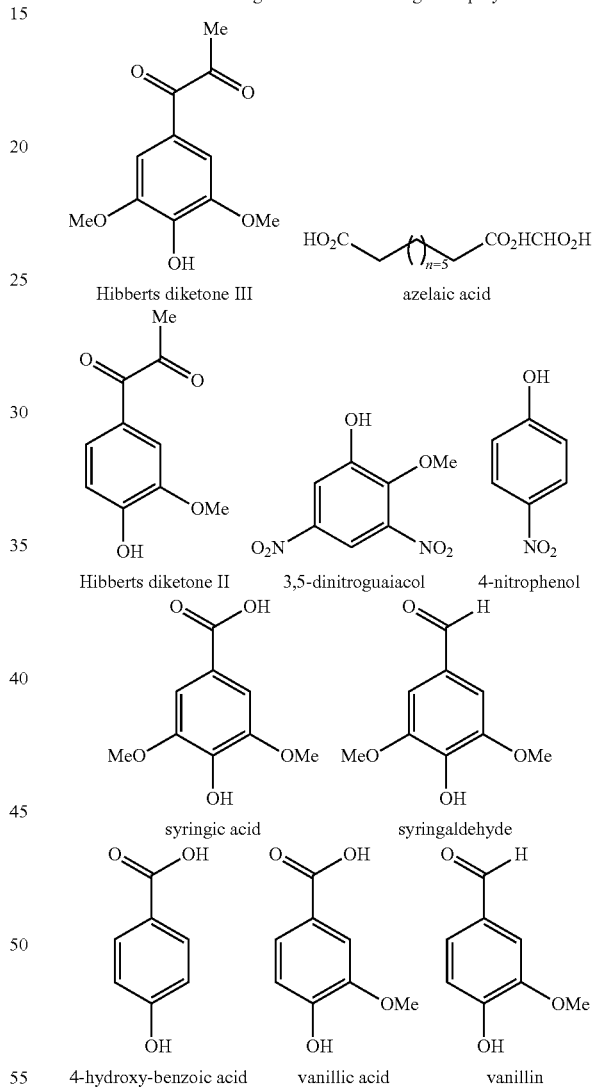

Chart 1. Low molecular weight chemicals from lignin depolymerization.

Hibberts diketone III
azelaic acid
Hibberts diketone II
3,5-dinitroguaiacol
4-nitrophenol
syringic acid
syringaldehyde
4-hydroxy-benzoic acid
vanillic acid
vanillin The products resulting from oxidation and subsequent cleavage of authentic lignin samples shown in Chart 1 were identified and then quantified by reverse phase HPLC-MS. A high resolution mass spectrometer acquired MS and MS/MS spectra in positive- and negative-ion mode, which were used to determine molecular formulas via exact mass measurement and to infer molecular structure by interpretation of MS/MS spectra. Candidate compounds' identities were confirmed by comparing retention times and MS/MS spectra against authentic standards that were either purchased or synthesized in-house. After identification of product mixture components, their concentrations were determined by analysis against a standard curve prepared from serial dilutions of an authentic standard of each identified component. Currently, 25 compounds can be quantified in one chromatographic run using a water: acetonitrile binary gradient, C18 column chemistry, and isotopically labeled vanillin as an internal standard.

What is claimed is:

1. A method to cleave C—C and C—O bonds in β-O-4 linkages in lignin or lignin sub-units, the method comprising:
   (a) oxidizing at least a portion of secondary benzylic alcohol groups in (β-O-4 linkages in the lignin or lignin sub-unit to corresponding ketones, resulting in an oxidized lignin or lignin sub-unit, wherein step (a) comprises contacting the lignin or lignin sub-unit with a catalyst comprising nitric acid ($HNO_3$) in combination with another Brønsted acid, in the absence of a metal-containing catalyst, thereby yielding the oxidized lignin or lignin sub-unit; and then
   (b) cleaving C—O or C—C bonds in the oxidized lignin or lignin sub-unit by reacting it with reagent selected from the group consisting of organic carboxylic acids, salts of organic carboxylic acids, and esters of organic carboxylic acids, for a time and a temperature at which at least a portion of β-O-4 linkages in the oxidized lignin or lignin sub-unit are cleaved.

2. The method of claim 1, comprising contacting the lignin or lignin sub-unit with a catalyst in a polar aprotic solvent.

3. The method of claim 2, wherein the solvent further comprises up to 20 wt % water.

4. The method of claim 1, wherein the solvent comprises a nitrile.

5. The method of claim 1, wherein the Brønsted acid is selected from the group consisting of hydrochloric acid (HCl), hydrobromic acid (HBr), hydrofluoric acid (HF), hydroiodic acid (HI), phosphoric acid ($H_3PO_4$), sulfuric acid ($H_2SO_4$), boric acid ($B(OH)_3$), tetrafluoroboric acid ($HBF_4$), perchloric acid ($HClO_4$), acetic acid ($CH_3C(O)$—OH), trifluoroacetic acid ($CF_3C(O)$—OH), methanesulfonic acid ($CH_3SO_3H$), solid acid resins containing sulfonic acid sites, and solid acid resins containing benzoic acid sites.

\* \* \* \* \*